United States Patent
Lang

(10) Patent No.: US 9,700,971 B2
(45) Date of Patent: *Jul. 11, 2017

(54) IMPLANT DEVICE AND METHOD FOR MANUFACTURE

(71) Applicant: ConforMIS, Inc., Bedford, MA (US)

(72) Inventor: Philipp Lang, Lexington, MA (US)

(73) Assignee: ConforMIS, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/134,064

(22) Filed: Dec. 19, 2013

(65) Prior Publication Data

US 2014/0109384 A1    Apr. 24, 2014

Related U.S. Application Data

(63) Continuation of application No. 12/031,239, filed on Feb. 14, 2008, now Pat. No. 8,617,242, which is a
(Continued)

(51) Int. Cl.
*B23P 19/04* (2006.01)
*A61F 2/30* (2006.01)
(Continued)

(52) U.S. Cl.
CPC .......... *B23P 19/04* (2013.01); *A61F 2/30756* (2013.01); *A61F 2/30942* (2013.01);
(Continued)

(58) Field of Classification Search
CPC ........ B23P 19/04; A61F 2/38; A61F 2/30756; A61F 2/30942; A61F 2310/000167;
(Continued)

(56) References Cited

U.S. PATENT DOCUMENTS 3,314,420 A   4/1967  Smith et al. .............. 128/92
3,605,123 A   9/1971  Hahn ........................ 3/1
(Continued)

FOREIGN PATENT DOCUMENTS

CN   86209787   11/1987   ........... A61F 2/38
CN   2305966    2/1999    ........... A61F 2/28
(Continued)

OTHER PUBLICATIONS

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.
(Continued)

*Primary Examiner* — Pedro Philogene
(74) *Attorney, Agent, or Firm* — Sunstein Kann Murphy & Timbers LLP

(57) ABSTRACT

A knee implant includes a femoral component having first and second femoral component surfaces. The first femoral component surface is for securing to a surgically prepared compartment of a distal end of a femur. The second femoral component surface is configured to replicate the femoral condyle. The knee implant further includes a tibial component having first and second tibial component surfaces. The first tibial component surface is for contacting a proximal surface of the tibia that is substantially uncut subchondral bone. At least a portion of the first tibial component surface is a mirror image of the proximal tibial surface. The second tibial component surface articulates with the second femoral component surface.

8 Claims, 2 Drawing Sheets

Related U.S. Application Data continuation-in-part of application No. 10/681,749, filed on Oct. 7, 2003, now Pat. No. 7,799,077, and a continuation-in-part of application No. 10/997,407, filed on Nov. 24, 2004, now Pat. No. 8,882,847, which is a continuation-in-part of application No. 10/752,438, filed on Jan. 5, 2004, now Pat. No. 8,545,569, which is a continuation-in-part of application No. 10/724,010, filed on Nov. 25, 2003, now Pat. No. 7,618,451, which is a continuation-in-part of application No. 10/305,652, filed on Nov. 27, 2002, now Pat. No. 7,468,075, which is a continuation-in-part of application No. 10/160,667, filed on May 28, 2002, said application No. 10/997,407 is a continuation-in-part of application No. 10/681,750, filed on Oct. 7, 2003.

(60) Provisional application No. 60/889,859, filed on Feb. 14, 2007, provisional application No. 60/416,601, filed on Oct. 7, 2002, provisional application No. 60/467,686, filed on May 2, 2003, provisional application No. 60/293,488, filed on May 25, 2001, provisional application No. 60/363,527, filed on Mar. 12, 2002, provisional application No. 60/380,695, filed on May 14, 2002, provisional application No. 60/380,692, filed on May 14, 2002.

(51) Int. Cl.
*A61F 2/38* (2006.01)
*G06F 17/50* (2006.01)
*A61F 2/32* (2006.01)
*A61F 2/40* (2006.01)
*A61F 2/42* (2006.01)
*A61F 2/44* (2006.01)

(52) U.S. Cl.
CPC .............. *A61F 2/38* (2013.01); *G06F 17/50* (2013.01); *A61F 2/32* (2013.01); *A61F 2/3804* (2013.01); *A61F 2/389* (2013.01); *A61F 2/3859* (2013.01); *A61F 2/40* (2013.01); *A61F 2/4202* (2013.01); *A61F 2/4225* (2013.01); *A61F 2/4241* (2013.01); *A61F 2/4261* (2013.01); *A61F 2/44* (2013.01); *A61F 2002/30092* (2013.01); *A61F 2002/3097* (2013.01); *A61F 2002/30884* (2013.01); *A61F 2002/30892* (2013.01); *A61F 2002/30952* (2013.01); *A61F 2002/30957* (2013.01); *A61F 2002/30968* (2013.01); *A61F 2210/0014* (2013.01); *A61F 2310/00011* (2013.01); *A61F 2310/00017* (2013.01); *A61F 2310/00023* (2013.01); *A61F 2310/00029* (2013.01); *A61F 2310/00131* (2013.01); *A61F 2310/00161* (2013.01); *A61F 2310/00167* (2013.01); *A61F 2310/00179* (2013.01); *A61F 2310/00203* (2013.01); *A61F 2310/00239* (2013.01); *Y10T 29/49995* (2015.01)

(58) Field of Classification Search
CPC .......... A61F 2310/00029; A61F 2/4202; A61F 2/3804; A61F 2/4261; A61F 2/3859; A61F 2/40; A61F 2/389; A61F 2/32; A61F 2/4225; A61F 2/44; A61F 2/4241; A61F 2002/30892; A61F 2002/30968; A61F 2002/30092; A61F 2002/3097; A61F 2002/30957; A61F 2002/30884; A61F 2002/30952; A61F 2210/0014; G06F 17/50; Y10T 29/49995
USPC ........ 128/898; 623/901, 13.11, 18.11, 19.11, 623/20.14, 17.16, 23.58, 20.29, 908; 264/222; 600/594, 589; 700/95–98, 118; 703/11; 29/557
See application file for complete search history.

(56) References Cited

U.S. PATENT DOCUMENTS

| | | | |
|---|---|---|---|
| 3,694,820 A | 10/1972 | Scales et al. | 3/1 |
| 3,798,679 A | 3/1974 | Ewald | 3/1 |
| 3,808,606 A | 5/1974 | Tronzo | 3/1 |
| 3,816,855 A | 6/1974 | Saleh | 3/1 |
| 3,843,975 A | 10/1974 | Tronzo | 3/1 |
| 3,852,830 A | 12/1974 | Marmor | 3/1 |
| 3,855,638 A | 12/1974 | Pilliar | 3/1 |
| 3,938,198 A | 2/1976 | Kahn et al. | 3/1.912 |
| 3,987,499 A | 10/1976 | Scharbach et al. | 3/1.91 |
| 3,991,425 A | 11/1976 | Martin et al. | 3/1.91 |
| 4,052,753 A | 10/1977 | Dedo | 3/1 |
| 4,055,862 A | 11/1977 | Farling | 3/1.91 |
| 4,085,466 A * | 4/1978 | Goodfellow et al. | 623/20.3 |
| 4,098,626 A | 7/1978 | Graham et al. | 149/19.4 |
| 4,164,793 A | 8/1979 | Swanson | 3/1.91 |
| 4,178,641 A | 12/1979 | Grundei et al. | 3/1.911 |
| 4,203,444 A | 5/1980 | Bonnell et al. | 128/276 |
| 4,207,627 A | 6/1980 | Cloutier | 3/1.911 |
| 4,211,228 A | 7/1980 | Cloutier | 128/303 R |
| 4,213,816 A | 7/1980 | Morris | 156/245 |
| 4,219,893 A | 9/1980 | Noiles | 3/1.911 |
| 4,280,231 A | 7/1981 | Swanson | 3/1.91 |
| 4,309,778 A | 1/1982 | Buechel et al. | 3/1.911 |
| 4,340,978 A | 7/1982 | Buechel et al. | 3/1.911 |
| 4,344,193 A | 8/1982 | Kenny | 3/1.911 |
| 4,368,040 A | 1/1983 | Weissman | 433/36 |
| 4,436,684 A | 3/1984 | White | 264/138 |
| 4,459,985 A | 7/1984 | McKay et al. | 128/303 R |
| 4,502,161 A | 3/1985 | Wall | 3/1.91 |
| 4,575,805 A | 3/1986 | Moermann et al. | 364/474 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,655,227 A | 4/1987 | Gracovetsky | 128/781 |
| 4,662,889 A | 5/1987 | Zichner et al. | 623/20 |
| 4,673,409 A | 6/1987 | Van Kampen | 623/23 |
| 4,699,156 A | 10/1987 | Gracovetsky | 128/781 |
| 4,714,472 A | 12/1987 | Averill et al. | 623/20 |
| 4,714,474 A | 12/1987 | Brooks, Jr. et al. | 623/20 |
| 4,769,040 A | 9/1988 | Wevers | 623/20 |
| 4,813,436 A | 3/1989 | Au | 128/779 |
| 4,822,365 A | 4/1989 | Walker et al. | 623/20 |
| 4,823,807 A | 4/1989 | Russell et al. | 128/773 |
| 4,846,835 A | 7/1989 | Grande | 623/11 |
| 4,865,607 A | 9/1989 | Witzel et al. | 623/20 |
| 4,872,452 A | 10/1989 | Alexson | 128/92 VJ |
| 4,880,429 A | 11/1989 | Stone | 623/18 |
| 4,883,488 A | 11/1989 | Bloebaum et al. | 3/20 |
| 4,888,021 A | 12/1989 | Forte et al. | 623/20 |
| 4,936,853 A | 6/1990 | Fabian et al. | 623/20 |
| 4,936,862 A | 6/1990 | Walker et al. | 623/23 |
| 4,944,757 A | 7/1990 | Martinez et al. | 623/20 |
| 5,019,103 A | 5/1991 | Van Zile et al. | 623/20 |
| 5,021,061 A | 6/1991 | Wevers et al. | 623/20 |
| 5,041,138 A | 8/1991 | Vacanti et al. | 623/16 |
| 5,047,057 A | 9/1991 | Lawes | 623/20 |
| 5,059,216 A | 10/1991 | Winters | 623/20 |
| 5,067,964 A | 11/1991 | Richmond et al. | 623/18 |
| 5,099,859 A | 3/1992 | Bell | 128/781 |
| 5,108,452 A | 4/1992 | Fallin | 623/23 |
| 5,123,927 A * | 6/1992 | Duncan et al. | 623/20.21 |
| 5,129,908 A | 7/1992 | Petersen | 606/88 |
| 5,133,759 A | 7/1992 | Turner | 623/20 |
| 5,150,304 A | 9/1992 | Berchem et al. | 364/474.24 |
| 5,152,797 A | 10/1992 | Luckman et al. | 623/20 |
| 5,154,178 A | 10/1992 | Shah | 128/653.2 |

(56) References Cited

U.S. PATENT DOCUMENTS

| | | | |
|---|---|---|---|
| 5,162,430 A | 11/1992 | Rhee et al. ................. 525/54.1 |
| 5,171,244 A | 12/1992 | Caspari et al. ................ 606/88 |
| 5,171,322 A | 12/1992 | Kenny ........................... 623/18 |
| 5,197,985 A | 3/1993 | Caplan et al. ................. 623/16 |
| 5,206,023 A | 4/1993 | Hunziker ...................... 424/423 |
| 5,226,914 A | 7/1993 | Caplan et al. ................. 623/16 |
| 5,234,433 A | 8/1993 | Bert et al. ...................... 606/88 |
| 5,245,282 A | 9/1993 | Mugler, III et al. .......... 324/309 |
| 5,246,013 A | 9/1993 | Frank et al. .................. 128/774 |
| 5,246,530 A | 9/1993 | Bugle et al. .................. 156/643 |
| 5,270,300 A | 12/1993 | Hunziker ...................... 514/12 |
| 5,274,565 A | 12/1993 | Reuben ................... 364/474.24 |
| 5,282,868 A | 2/1994 | Bahler ........................... 623/20 |
| 5,288,797 A | 2/1994 | Khalil et al. .................. 524/872 |
| 5,303,148 A | 4/1994 | Mattson et al. .......... 364/413.01 |
| 5,306,307 A | 4/1994 | Senter et al. ................... 623/17 |
| 5,306,311 A | 4/1994 | Stone et al. ................... 623/18 |
| 5,314,478 A | 5/1994 | Oka et al. ...................... 623/18 |
| 5,314,482 A | 5/1994 | Goodfellow et al. ......... 623/20 |
| 5,320,102 A | 6/1994 | Paul et al. ................. 128/653.2 |
| 5,326,363 A | 7/1994 | Aikins ........................... 623/20 |
| 5,326,365 A | 7/1994 | Alvine ........................... 623/21 |
| 5,344,459 A | 9/1994 | Swartz .......................... 623/18 |
| 5,360,446 A | 11/1994 | Kennedy ....................... 623/16 |
| 5,365,996 A | 11/1994 | Crook ............................ 164/45 |
| 5,368,858 A | 11/1994 | Hunziker ...................... 424/423 |
| 5,403,319 A | 4/1995 | Matsen, III et al. ........... 606/88 |
| 5,405,395 A | 4/1995 | Coates ........................... 623/20 |
| 5,413,116 A | 5/1995 | Radke et al. ................. 128/777 |
| 5,423,828 A | 6/1995 | Benson ......................... 606/102 |
| 5,433,215 A | 7/1995 | Athanasiou et al. ......... 128/774 |
| 5,445,152 A | 8/1995 | Bell et al. .................. 128/653.5 |
| 5,448,489 A | 9/1995 | Reuben ................... 364/474.05 |
| 5,468,787 A | 11/1995 | Braden et al. ................ 523/113 |
| 5,478,739 A | 12/1995 | Slivka et al. ............ 435/240.23 |
| 5,489,309 A | 2/1996 | Lackey et al. ................. 623/20 |
| 5,501,687 A | 3/1996 | Willert et al. .................. 606/94 |
| 5,503,162 A | 4/1996 | Athanasiou et al. ......... 128/774 |
| 5,507,820 A | 4/1996 | Pappas .......................... 623/20 |
| 5,510,121 A | 4/1996 | Rhee et al. ................... 424/520 |
| 5,522,900 A | 6/1996 | Hollister ....................... 623/18 |
| 5,523,843 A | 6/1996 | Yamane et al. ............... 356/363 |
| 5,541,515 A | 7/1996 | Tsujita .......................... 324/318 |
| 5,549,690 A | 8/1996 | Hollister et al. ............... 623/21 |
| 5,554,190 A | 9/1996 | Draenert ....................... 623/16 |
| 5,556,432 A | 9/1996 | Kubein-Meesenburg et al. .............................. 623/20 |
| 5,560,096 A | 10/1996 | Stephens ....................... 29/558 |
| 5,564,437 A | 10/1996 | Bainville et al. ............. 128/774 |
| 5,571,191 A | 11/1996 | Fitz ................................ 623/17 |
| 5,571,205 A | 11/1996 | James ........................... 623/24 |
| 5,609,640 A | 3/1997 | Johnson ........................ 623/20 |
| 5,611,802 A | 3/1997 | Samuelson et al. ........... 606/86 |
| 5,616,146 A | 4/1997 | Murray ........................ 606/80 |
| 5,632,745 A | 5/1997 | Schwartz ...................... 606/75 |
| 5,671,741 A | 9/1997 | Lang et al. ................. 128/653.2 |
| 5,681,354 A | 10/1997 | Eckhoff ......................... 623/20 |
| 5,682,886 A | 11/1997 | Delp et al. ................. 128/653.1 |
| 5,683,466 A | 11/1997 | Vitale ............................ 623/18 |
| 5,683,468 A | 11/1997 | Pappas .......................... 623/20 |
| 5,684,562 A | 11/1997 | Fujieda ......................... 351/212 |
| 5,687,210 A | 11/1997 | Maitrejean et al. ........... 378/57 |
| 5,690,635 A | 11/1997 | Matsen, III et al. ........... 606/88 |
| 5,702,463 A | 12/1997 | Pothier et al. .................. 623/20 |
| 5,723,331 A | 3/1998 | Tubo et al. ................... 435/366 |
| 5,728,162 A | 3/1998 | Eckhoff ......................... 623/20 |
| 5,735,277 A | 4/1998 | Schuster .................... 128/653.1 |
| 5,749,362 A | 5/1998 | Funda et al. ............... 128/653.1 |
| 5,749,874 A | 5/1998 | Schwartz ...................... 606/75 |
| 5,749,876 A | 5/1998 | Duvillier et al. ............... 606/88 |
| 5,759,205 A | 6/1998 | Valentini ....................... 623/16 |
| 5,768,134 A | 6/1998 | Swaelens et al. ....... 364/468.28 |
| 5,769,899 A | 6/1998 | Schwartz et al. .............. 623/18 |
| 5,772,595 A | 6/1998 | Votruba et al. ............... 600/415 |
| 5,779,651 A | 7/1998 | Buschmann et al. ......... 600/587 |
| 5,786,217 A | 7/1998 | Tubo et al. ................... 435/402 |
| 5,810,006 A | 9/1998 | Votruba et al. ............ 128/653.2 |
| 5,824,085 A | 10/1998 | Sahay et al. ................... 623/16 |
| 5,824,102 A | 10/1998 | Buscayret ..................... 623/20 |
| 5,827,289 A | 10/1998 | Reiley et al. .................. 606/86 |
| 5,832,422 A | 11/1998 | Wiedenhoefer .............. 702/154 |
| 5,835,619 A | 11/1998 | Morimoto et al. ........... 382/132 |
| 5,842,477 A | 12/1998 | Naughton et al. ............ 128/898 |
| 5,847,804 A | 12/1998 | Sarver et al. ................. 351/206 |
| 5,853,746 A | 12/1998 | Hunziker ...................... 424/426 |
| 5,871,018 A | 2/1999 | Delp et al. .................... 128/898 |
| 5,871,540 A | 2/1999 | Weissman et al. ............ 623/20 |
| 5,871,542 A | 2/1999 | Goodfellow et al. .......... 623/20 |
| 5,871,546 A | 2/1999 | Colleran et al. ............... 623/20 |
| 5,879,390 A | 3/1999 | Kubein-Meesenburg et al. .............................. 623/20 |
| 5,880,976 A | 3/1999 | DiGioia, III et al. ......... 364/578 |
| 5,885,296 A | 3/1999 | Masini ........................... 606/86 |
| 5,885,298 A | 3/1999 | Herrington et al. ............ 606/88 |
| 5,897,559 A | 4/1999 | Masini ........................... 606/86 |
| 5,899,859 A | 5/1999 | Votruba et al. ............... 600/415 |
| 5,900,245 A | 5/1999 | Sawhney et al. ............. 424/426 |
| 5,906,643 A | 5/1999 | Walker .......................... 623/20 |
| 5,906,934 A | 5/1999 | Grande et al. ................ 435/325 |
| 5,913,821 A | 6/1999 | Farese et al. ................. 600/425 |
| 5,916,220 A | 6/1999 | Masini ........................... 606/88 |
| 5,928,945 A | 7/1999 | Seliktar et al. ............... 435/395 |
| 5,939,323 A | 8/1999 | Valentini et al. ............. 435/395 |
| 5,961,523 A | 10/1999 | Masini ........................... 606/86 |
| 5,968,051 A | 10/1999 | Luckman et al. .............. 606/88 |
| 5,968,099 A | 10/1999 | Badorf et al. .................. 623/20 |
| 5,972,385 A | 10/1999 | Liu et al. ...................... 424/486 |
| 5,995,738 A | 11/1999 | DiGioia, III et al. ... 395/500.32 |
| 6,002,859 A | 12/1999 | DiGioia, III et al. ... 395/500.32 |
| 6,013,103 A | 1/2000 | Kaufman et al. .............. 623/20 |
| 6,046,379 A | 4/2000 | Stone et al. .................... 623/11 |
| 6,057,927 A | 5/2000 | Levesque et al. ........ 356/432 T |
| 6,078,680 A | 6/2000 | Yoshida et al. .............. 382/128 |
| 6,081,577 A | 6/2000 | Webber ......................... 378/23 |
| 6,082,364 A | 7/2000 | Balian et al. ................. 128/898 |
| 6,090,144 A | 7/2000 | Letot et al. .................... 623/20 |
| 6,093,204 A | 7/2000 | Stone ........................ 623/14.12 |
| 6,102,916 A | 8/2000 | Masini ........................... 606/88 |
| 6,102,955 A | 8/2000 | Mendes et al. ................ 623/20 |
| 6,110,209 A | 8/2000 | Stone ........................ 623/16.11 |
| 6,112,109 A | 8/2000 | D'Urso ......................... 600/407 |
| 6,120,541 A | 9/2000 | Johnson ................... 623/14.12 |
| 6,120,543 A | 9/2000 | Kubein-Meesenburg et al. .............................. 623/20 |
| 6,126,690 A | 10/2000 | Ateshian et al. ............... 623/18 |
| 6,139,578 A | 10/2000 | Lee et al. .................. 623/16.11 |
| 6,146,422 A | 11/2000 | Lawson .................... 623/17.16 |
| 6,151,521 A | 11/2000 | Guo et al. ..................... 600/407 |
| 6,152,960 A | 11/2000 | Pappas ..................... 623/20.31 |
| 6,156,069 A | 12/2000 | Amstutz .................... 623/22.11 |
| 6,161,080 A | 12/2000 | Aouni-Ateshian et al. ..... 703/11 |
| 6,162,208 A | 12/2000 | Hipps .............................. 606/1 |
| 6,165,221 A | 12/2000 | Schmotzer ............... 623/20.11 |
| 6,171,340 B1 | 1/2001 | McDowell ................ 623/18.11 |
| 6,175,655 B1 | 1/2001 | George, III et al. .......... 382/257 |
| 6,178,225 B1 | 1/2001 | Zur et al. ..................... 378/98.2 |
| 6,187,010 B1 | 2/2001 | Masini ........................... 606/86 |
| 6,197,064 B1 | 3/2001 | Haines et al. ............. 623/20.31 |
| 6,197,325 B1 | 3/2001 | MacPhee et al. ............. 424/426 |
| 6,200,606 B1 | 3/2001 | Peterson et al. .............. 424/574 |
| 6,203,576 B1 | 3/2001 | Afriat et al. ............... 623/20.27 |
| 6,205,411 B1 | 3/2001 | DiGioia, III et al. ........... 703/11 |
| 6,206,927 B1 | 3/2001 | Fell et al. .................. 623/20.29 |
| 6,214,369 B1 | 4/2001 | Grande et al. ................ 424/423 |
| 6,217,894 B1 | 4/2001 | Sawhney et al. ............. 424/426 |
| 6,219,571 B1 | 4/2001 | Hargreaves et al. ......... 600/410 |
| 6,224,632 B1 | 5/2001 | Pappas et al. ............ 623/20.34 |
| 6,235,060 B1 | 5/2001 | Kubein-Meesenburg et al. .......................... 623/20.31 |
| 6,249,692 B1 | 6/2001 | Cowin .......................... 600/407 |
| 6,251,143 B1 | 6/2001 | Schwartz et al. .......... 623/23.72 |
| 6,254,639 B1 | 7/2001 | Peckitt ...................... 623/11.11 |
| 6,261,296 B1 | 7/2001 | Aebi et al. ..................... 606/90 |
| 6,277,151 B1 | 8/2001 | Lee et al. .................. 623/23.61 |

(56) References Cited

U.S. PATENT DOCUMENTS

| | | | |
|---|---|---|---|
| 6,280,478 B1 | 8/2001 | Richter et al. | 623/23.56 |
| 6,281,195 B1 | 8/2001 | Rueger et al. | 514/21 |
| 6,283,980 B1 | 9/2001 | Vibe-Hansen et al. | 606/151 |
| 6,289,115 B1 | 9/2001 | Takeo | 382/130 |
| 6,289,753 B1 | 9/2001 | Basser et al. | 73/866 |
| 6,299,645 B1 | 10/2001 | Ogden | 623/20.21 |
| 6,299,905 B1 | 10/2001 | Peterson et al. | 424/486 |
| 6,302,582 B1 | 10/2001 | Nord et al. | 378/207 |
| 6,310,477 B1 | 10/2001 | Schneider | 324/307 |
| 6,310,619 B1 | 10/2001 | Rice | 345/420 |
| 6,316,153 B1 | 11/2001 | Goodman et al. | 430/8 |
| 6,319,712 B1 | 11/2001 | Meenen et al. | 435/395 |
| 6,322,588 B1 | 11/2001 | Ogle et al. | 623/1.46 |
| 6,328,765 B1 | 12/2001 | Hardwick et al. | 623/23.72 |
| 6,334,006 B1 | 12/2001 | Tanabe | 385/12 |
| 6,334,066 B1 | 12/2001 | Rupprecht et al. | 600/411 |
| 6,342,075 B1 | 1/2002 | MacArthur | 623/20.14 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,379,388 B1 | 4/2002 | Ensign et al. | 623/20.34 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,402,786 B1 | 6/2002 | Insall et al. | 623/20.35 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,450,978 B1 | 9/2002 | Brosseau et al. | 600/595 |
| 6,459,948 B1 | 10/2002 | Ateshian et al. | 700/117 |
| 6,468,314 B2 | 10/2002 | Schwartz et al. | 623/23.72 |
| 6,479,996 B1 | 11/2002 | Hoogeveen et al. | 324/309 |
| 6,482,209 B1 | 11/2002 | Engh et al. | 606/79 |
| 6,510,334 B1 | 1/2003 | Schuster et al. | 600/407 |
| 6,514,514 B1 | 2/2003 | Atkinson et al. | 424/423 |
| 6,520,964 B2 | 2/2003 | Tallarida et al. | 396/567 |
| 6,533,737 B1 | 3/2003 | Brosseau et al. | 600/595 |
| 6,540,786 B2 * | 4/2003 | Chibrac | A61F 2/3804 623/18.11 |
| 6,556,855 B2 | 4/2003 | Thesen | 600/419 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,591,581 B2 | 7/2003 | Schmieding | 53/396 |
| 6,592,624 B1 | 7/2003 | Fraser et al. | 623/17.16 |
| 6,623,526 B1 | 9/2003 | Lloyd | 623/20.28 |
| 6,626,945 B2 | 9/2003 | Simon et al. | 623/17.19 |
| 6,632,235 B2 | 10/2003 | Weikel et al. | 606/192 |
| 6,632,246 B1 | 10/2003 | Simon et al. | 623/14.12 |
| 6,652,587 B2 | 11/2003 | Felt et al. | 623/20.16 |
| 6,679,917 B2 | 1/2004 | Ek | 623/20.14 |
| 6,690,816 B2 | 2/2004 | Aylward et al. | 382/128 |
| 6,692,448 B2 | 2/2004 | Tanaka et al. | 600/587 |
| 6,702,821 B2 | 3/2004 | Bonutti | 606/88 |
| 6,712,856 B1 | 3/2004 | Carignan et al. | 623/20.35 |
| 6,719,794 B2 | 4/2004 | Gerber et al. | 623/17.11 |
| 6,770,078 B2 | 8/2004 | Bonutti | 606/86 |
| 6,772,026 B2 | 8/2004 | Bradbury et al. | 700/98 |
| 6,799,066 B2 | 9/2004 | Steines et al. | 600/407 |
| 6,816,607 B2 | 11/2004 | O'Donnell et al. | 382/131 |
| 6,835,377 B2 | 12/2004 | Goldberg et al. | 424/93.7 |
| 6,855,165 B2 | 2/2005 | Fell et al. | 623/14.12 |
| 6,873,741 B2 | 3/2005 | Li | 382/266 |
| 6,893,463 B2 | 5/2005 | Fell et al. | 623/14.12 |
| 6,893,467 B1 | 5/2005 | Bercovy | 623/20.14 |
| 6,902,582 B2 | 6/2005 | Kubein-Meesenburg et al. | 623/20.31 |
| 6,905,514 B2 | 6/2005 | Carignan et al. | 623/20.35 |
| 6,911,044 B2 | 6/2005 | Fell et al. | 623/14.12 |
| 6,916,341 B2 | 7/2005 | Rolston | 623/20.3 |
| 6,923,831 B2 | 8/2005 | Fell et al. | 623/14.12 |
| 6,932,842 B1 | 8/2005 | Litschko et al. | 623/16.11 |
| 6,964,687 B1 | 11/2005 | Bernard et al. | 623/17.16 |
| 6,966,928 B2 | 11/2005 | Fell et al. | 623/14.12 |
| 6,978,188 B1 | 12/2005 | Christensen | 700/118 |
| 6,984,981 B2 | 1/2006 | Tamez-Peña et al. | 324/309 |
| 6,998,841 B1 | 2/2006 | Tamez-Peña et al. | 324/302 |
| 7,001,672 B2 | 2/2006 | Justin et al. | 428/615 |
| 7,020,314 B1 | 3/2006 | Suri et al. | 382/130 |
| 7,050,534 B2 | 5/2006 | Lang | 378/54 |
| 7,058,159 B2 | 6/2006 | Lang et al. | 378/54 |
| 7,058,209 B2 | 6/2006 | Chen et al. | 382/117 |
| 7,060,101 B2 | 6/2006 | O'Connor et al. | 623/20.32 |
| 7,105,026 B2 | 9/2006 | Johnson et al. | 623/20.14 |
| 7,115,131 B2 | 10/2006 | Engh et al. | 606/79 |
| 7,172,596 B2 | 2/2007 | Coon et al. | 606/87 |
| 7,174,282 B2 | 2/2007 | Hollister et al. | 703/2 |
| 7,184,814 B2 | 2/2007 | Lang et al. | 600/416 |
| 7,204,807 B2 | 4/2007 | Tsoref | 600/438 |
| 7,238,203 B2 | 7/2007 | Bagga et al. | 623/17.11 |
| 7,239,908 B1 | 7/2007 | Alexander et al. | 600/427 |
| 7,244,273 B2 | 7/2007 | Pedersen et al. | 623/14.12 |
| 7,245,697 B2 | 7/2007 | Lang | 378/54 |
| 7,292,674 B2 | 11/2007 | Lang | 378/54 |
| 7,326,252 B2 | 2/2008 | Otto et al. | 623/20.15 |
| 7,368,065 B2 | 5/2008 | Yang et al. | 216/83 |
| 7,379,529 B2 | 5/2008 | Lang | 378/54 |
| 7,438,685 B2 | 10/2008 | Burdette et al. | 600/439 |
| 7,445,640 B2 | 11/2008 | Despres, III et al. | 623/23.53 |
| 7,467,892 B2 | 12/2008 | Lang et al. | 378/207 |
| 7,468,075 B2 | 12/2008 | Lang et al. | 623/16.11 |
| 7,517,358 B2 | 4/2009 | Petersen | 606/247 |
| 7,520,901 B2 | 4/2009 | Engh et al. | 623/20.21 |
| 7,534,263 B2 | 5/2009 | Burdulis, Jr. et al. | 623/14.12 |
| 7,572,293 B2 | 8/2009 | Rhodes et al. | 623/20.32 |
| 7,603,192 B2 | 10/2009 | Martin et al. | 700/98 |
| 7,611,519 B2 | 11/2009 | Lefevre et al. | 606/102 |
| 7,611,653 B1 | 11/2009 | Elsner et al. | 264/255 |
| 7,615,054 B1 | 11/2009 | Bonutti | 606/88 |
| 7,618,451 B2 | 11/2009 | Berez et al. | 623/14.12 |
| 7,632,575 B2 | 12/2009 | Justin et al. | 428/615 |
| 7,634,119 B2 | 12/2009 | Tsougarakis et al. | 382/128 |
| 7,718,109 B2 | 5/2010 | Robb et al. | 264/308 |
| 7,796,791 B2 | 9/2010 | Tsougarakis et al. | 382/128 |
| 7,799,077 B2 | 9/2010 | Lang et al. | 623/14.12 |
| 7,806,896 B1 | 10/2010 | Bonutti | 606/86 R |
| 7,842,092 B2 | 11/2010 | Otto et al. | 623/18.11 |
| 7,881,768 B2 | 2/2011 | Lang et al. | 600/407 |
| 7,914,582 B2 | 3/2011 | Felt et al. | 623/20.16 |
| 7,935,151 B2 | 5/2011 | Haines | 623/20.35 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,070,821 B2 | 12/2011 | Roger | 623/20.17 |
| 8,077,950 B2 | 12/2011 | Tsougarakis et al. | 382/128 |
| 8,083,745 B2 | 12/2011 | Lang et al. | 606/87 |
| 8,086,336 B2 | 12/2011 | Christensen | 700/98 |
| 8,094,900 B2 | 1/2012 | Steines et al. | 382/128 |
| 8,105,330 B2 | 1/2012 | Fitz et al. | 606/88 |
| 8,112,142 B2 | 2/2012 | Alexander et al. | 600/407 |
| RE43,282 E | 3/2012 | Alexander et al. | 600/427 |
| 8,192,498 B2 | 6/2012 | Wagner et al. | 623/20.21 |
| 8,211,181 B2 | 7/2012 | Walker | 623/20.21 |
| 8,234,097 B2 | 7/2012 | Steines et al. | 703/1 |
| 8,236,061 B2 | 8/2012 | Heldreth et al. | 623/20.31 |
| 8,265,730 B2 | 9/2012 | Alexander et al. | 600/410 |
| 8,306,601 B2 | 11/2012 | Lang et al. | 600/407 |
| 8,311,306 B2 | 11/2012 | Pavlovskaia et al. | 382/131 |
| 8,337,501 B2 | 12/2012 | Fitz et al. | 606/86 R |
| 8,337,507 B2 | 12/2012 | Lang et al. | 606/102 |
| 8,337,508 B2 | 12/2012 | Lavallee et al. | 606/105 |
| 8,343,218 B2 | 1/2013 | Lang et al. | 623/16.11 |
| 8,361,076 B2 | 1/2013 | Roose et al. | 606/88 |
| 8,366,771 B2 | 2/2013 | Burdulis, Jr. et al. | 623/14.12 |
| 8,369,926 B2 | 2/2013 | Lang et al. | 600/407 |

(56) References Cited

U.S. PATENT DOCUMENTS

| | | |
|---|---|---|
| 8,377,073 B2 | 2/2013 | Wasielewski .................. 606/102 |
| 8,377,129 B2 | 2/2013 | Fitz et al. .................. 623/14.12 |
| 8,380,471 B2 | 2/2013 | Iannotti et al. .................. 703/6 |
| 8,407,067 B2 | 3/2013 | Uthgenannt et al. ............. 705/2 |
| 8,439,926 B2 | 5/2013 | Bojarski et al. .................. 606/88 |
| 8,457,930 B2 | 6/2013 | Schroeder .......................... 703/1 |
| 8,460,304 B2 | 6/2013 | Fitz et al. ....................... 606/88 |
| 8,473,305 B2 | 6/2013 | Belcher et al. .................... 705/2 |
| 8,480,754 B2 | 7/2013 | Bojarski et al. ............. 623/20.35 |
| 8,486,150 B2 | 7/2013 | White et al. ................. 623/20.21 |
| 8,500,740 B2 | 8/2013 | Bojarski et al. ............. 606/86 R |
| 8,521,492 B2 | 8/2013 | Otto et al. ........................ 703/6 |
| 8,529,568 B2 | 9/2013 | Bouadi .............................. 606/84 |
| 8,529,630 B2 | 9/2013 | Bojarski et al. ............. 623/20.14 |
| 8,532,807 B2 | 9/2013 | Metzger .............................. 700/98 |
| 8,545,569 B2 | 10/2013 | Fitz et al. .................. 623/20.14 |
| 8,551,099 B2 | 10/2013 | Lang et al. .................. 606/86 R |
| 8,551,102 B2 | 10/2013 | Fitz et al. ....................... 606/88 |
| 8,551,103 B2 | 10/2013 | Fitz et al. ....................... 606/88 |
| 8,551,169 B2 | 10/2013 | Fitz et al. .................. 623/14.12 |
| 8,556,906 B2 | 10/2013 | Fitz et al. ....................... 606/87 |
| 8,556,907 B2 | 10/2013 | Fitz et al. ....................... 606/87 |
| 8,556,971 B2 | 10/2013 | Lang .............................. 623/14.12 |
| 8,556,983 B2 | 10/2013 | Bojarski et al. ............. 623/20.35 |
| 8,561,278 B2 | 10/2013 | Fitz et al. .................. 29/407.09 |
| 8,562,611 B2 | 10/2013 | Fitz et al. ....................... 606/80 |
| 8,562,618 B2 | 10/2013 | Fitz et al. ....................... 606/88 |
| 8,568,479 B2 | 10/2013 | Fitz et al. .................. 623/14.12 |
| 8,568,480 B2 | 10/2013 | Fitz et al. .................. 623/14.12 |
| 8,617,172 B2 | 12/2013 | Fitz et al. ....................... 606/88 |
| 8,617,242 B2 * | 12/2013 | Philipp ............... A61F 2/30756 |
| | | 623/18.11 |
| 8,623,026 B2 | 1/2014 | Wong et al. ..................... 606/96 |
| 8,634,617 B2 | 1/2014 | Tsougarakis et al. ......... 382/128 |
| 8,638,998 B2 | 1/2014 | Steines et al. ................. 382/128 |
| 8,641,716 B2 | 2/2014 | Fitz et al. ....................... 606/80 |
| 8,657,827 B2 | 2/2014 | Fitz et al. ....................... 606/87 |
| 8,682,052 B2 | 3/2014 | Fitz et al. ....................... 382/131 |
| 8,690,945 B2 | 4/2014 | Fitz et al. .................. 623/16.11 |
| 8,709,089 B2 | 4/2014 | Lang et al. .................. 623/18.11 |
| 8,735,773 B2 | 5/2014 | Lang .......................... 219/121.72 |
| 8,768,028 B2 | 7/2014 | Lang et al. ..................... 382/131 |
| 8,771,365 B2 | 7/2014 | Bojarski et al. ............. 623/20.32 |
| 9,408,686 B1 | 8/2016 | Miller et al. |
| 9,439,767 B2 | 9/2016 | Bojarski et al. ............. 606/86 R |
| 9,517,134 B2 | 12/2016 | Lang ........................... 606/86 R |
| 2001/0001120 A1 | 5/2001 | Masini .............................. 606/86 |
| 2001/0010023 A1 | 7/2001 | Schwartz et al. ............. 623/23.72 |
| 2001/0039455 A1 | 11/2001 | Simon et al. ................. 623/23.51 |
| 2002/0013626 A1 | 1/2002 | Geistlich et al. ............. 623/23.57 |
| 2002/0016543 A1 | 2/2002 | Tyler ................................ 600/410 |
| 2002/0022884 A1 | 2/2002 | Mansmann ................. 623/14.12 |
| 2002/0045940 A1 | 4/2002 | Giannetti et al. ............. 623/11.11 |
| 2002/0052606 A1 | 5/2002 | Bonutti ............................. 606/88 |
| 2002/0059049 A1 | 5/2002 | Bradbury et al. ............... 703/11 |
| 2002/0067798 A1 | 6/2002 | Lang et al. ....................... 378/54 |
| 2002/0068979 A1 | 6/2002 | Brown et al. ................... 623/20.3 |
| 2002/0072821 A1 | 6/2002 | Baker ................................. 700/98 |
| 2002/0079601 A1 | 6/2002 | Russell et al. .................. 264/40.1 |
| 2002/0082703 A1 | 6/2002 | Repicci ......................... 623/20.29 |
| 2002/0082741 A1 | 6/2002 | Mazumder et al. ........... 700/123 |
| 2002/0087274 A1 | 7/2002 | Alexander et al. ............. 702/19 |
| 2002/0106625 A1 | 8/2002 | Hung et al. ..................... 435/1.1 |
| 2002/0111694 A1 | 8/2002 | Ellingsen et al. .......... 623/23.57 |
| 2002/0115647 A1 | 8/2002 | Halvorsen et al. ............ 514/171 |
| 2002/0120274 A1 | 8/2002 | Overaker et al. ................ 606/72 |
| 2002/0120281 A1 | 8/2002 | Overaker .......................... 606/151 |
| 2002/0127264 A1 | 9/2002 | Felt et al. ......................... 424/423 |
| 2002/0133230 A1 | 9/2002 | Repicci ......................... 623/14.12 |
| 2002/0147392 A1 | 10/2002 | Steines et al. .................. 600/407 |
| 2002/0151986 A1 | 10/2002 | Asculai et al. ................... 424/484 |
| 2002/0156150 A1 | 10/2002 | Williams et al. ............... 523/113 |
| 2002/0173852 A1 | 11/2002 | Felt et al. ................... 623/20.32 |
| 2002/0177770 A1 | 11/2002 | Lang et al. .................... 600/410 |
| 2002/0183850 A1 | 12/2002 | Felt et al. ................... 623/20.16 |
| 2003/0015208 A1 | 1/2003 | Lang et al. .................... 128/922 |
| 2003/0031292 A1 | 2/2003 | Lang ................................ 378/54 |
| 2003/0035773 A1 | 2/2003 | Totterman et al. ............. 424/9.1 |
| 2003/0045935 A1 | 3/2003 | Angelucci et al. ........... 623/17.11 |
| 2003/0055500 A1 | 3/2003 | Fell et al. .................... 623/14.12 |
| 2003/0055501 A1 | 3/2003 | Fell et al. .................... 623/14.12 |
| 2003/0055502 A1 | 3/2003 | Lang et al. .................. 623/16.11 |
| 2003/0060882 A1 | 3/2003 | Fell et al. .................... 623/14.12 |
| 2003/0060883 A1 | 3/2003 | Fell et al. .................... 623/14.12 |
| 2003/0060884 A1 | 3/2003 | Fell et al. .................... 623/14.12 |
| 2003/0060885 A1 | 3/2003 | Fell et al. .................... 623/14.12 |
| 2003/0063704 A1 | 4/2003 | Lang ................................ 378/54 |
| 2003/0069591 A1 | 4/2003 | Carson et al. .................. 606/130 |
| 2003/0080957 A1 | 5/2003 | Stewart et al. ................. 345/420 |
| 2003/0100953 A1 | 5/2003 | Rosa et al. ................... 623/20.3 |
| 2003/0158606 A1 | 8/2003 | Coon et al. ................... 623/20.15 |
| 2003/0216669 A1 | 11/2003 | Lang et al. ...................... 600/587 |
| 2003/0225457 A1 | 12/2003 | Justin et al. ................. 623/20.14 |
| 2003/0236473 A1 * | 12/2003 | Dore ................... A61B 5/1077 |
| | | 600/587 |
| 2004/0006393 A1 | 1/2004 | Burkinshaw ................. 623/20.3 |
| 2004/0062358 A1 | 4/2004 | Lang et al. ..................... 378/207 |
| 2004/0081287 A1 | 4/2004 | Lang et al. ..................... 378/210 |
| 2004/0098132 A1 | 5/2004 | Andriacchi et al. ........ 623/20.35 |
| 2004/0098133 A1 | 5/2004 | Carignan et al. .......... 623/20.35 |
| 2004/0102851 A1 | 5/2004 | Saladino ..................... 623/20.15 |
| 2004/0102852 A1 | 5/2004 | Johnson et al. ............. 623/20.15 |
| 2004/0102866 A1 | 5/2004 | Harris et al. ................. 623/20.35 |
| 2004/0117015 A1 * | 6/2004 | Biscup ............... A61F 2/30942 |
| | | 623/16.11 |
| 2004/0117023 A1 | 6/2004 | Gerbec et al. ............. 623/18.11 |
| 2004/0122521 A1 | 6/2004 | Lee et al. ................... 623/20.15 |
| 2004/0133276 A1 | 7/2004 | Lang et al. .................. 623/14.12 |
| 2004/0138754 A1 | 7/2004 | Lang et al. .................. 623/20.14 |
| 2004/0138755 A1 | 7/2004 | O'Connor et al. .......... 623/20.32 |
| 2004/0147927 A1 | 7/2004 | Tsougarakis et al. ........... 606/53 |
| 2004/0153079 A1 | 8/2004 | Tsougarakis et al. ........... 606/77 |
| 2004/0153162 A1 | 8/2004 | Sanford et al. ............. 623/20.3 |
| 2004/0153164 A1 | 8/2004 | Sanford et al. ............ 623/20.29 |
| 2004/0167390 A1 | 8/2004 | Alexander et al. ........... 600/410 |
| 2004/0167630 A1 | 8/2004 | Rolston ...................... 623/20.14 |
| 2004/0193280 A1 | 9/2004 | Webster et al. ............. 623/20.33 |
| 2004/0204644 A1 | 10/2004 | Tsougarakis et al. ........ 600/410 |
| 2004/0204760 A1 | 10/2004 | Fitz et al. .................... 623/14.12 |
| 2004/0204766 A1 | 10/2004 | Siebel ............................ 623/20.31 |
| 2004/0236424 A1 | 11/2004 | Berez et al. ................. 623/14.12 |
| 2005/0010106 A1 | 1/2005 | Lang et al. ...................... 600/425 |
| 2005/0015153 A1 | 1/2005 | Goble et al. ................. 623/23.46 |
| 2005/0021042 A1 | 1/2005 | Marnay et al. .................. 606/99 |
| 2005/0033424 A1 | 2/2005 | Fell ............................... 623/14.12 |
| 2005/0043807 A1 | 2/2005 | Wood ........................... 623/20.14 |
| 2005/0055028 A1 | 3/2005 | Haines ............................ 606/79 |
| 2005/0078802 A1 | 4/2005 | Lang et al. ..................... 387/207 |
| 2005/0107883 A1 | 5/2005 | Goodfried et al. .......... 623/20.15 |
| 2005/0107884 A1 | 5/2005 | Johnson et al. ............. 623/20.15 |
| 2005/0119664 A1 | 6/2005 | Carignan et al. ............... 606/96 |
| 2005/0125029 A1 | 6/2005 | Bernard et al. ................. 606/205 |
| 2005/0148843 A1 | 7/2005 | Roose .............................. 700/117 |
| 2005/0154471 A1 | 7/2005 | Aram et al. ................. 623/20.15 |
| 2005/0171612 A1 | 8/2005 | Rolston ...................... 623/20.19 |
| 2005/0203384 A1 | 9/2005 | Sati et al. ...................... 600/426 |
| 2005/0216305 A1 | 9/2005 | Funderud .......................... 705/2 |
| 2005/0226374 A1 | 10/2005 | Lang et al. ..................... 378/54 |
| 2005/0234461 A1 | 10/2005 | Burdulis, Jr. et al. .......... 606/79 |
| 2005/0244239 A1 | 11/2005 | Shimp ............................ 409/132 |
| 2005/0267584 A1 | 12/2005 | Burdulis, Jr. et al. ..... 623/20.19 |
| 2005/0278034 A1 | 12/2005 | Johnson et al. ............. 623/20.15 |
| 2006/0009853 A1 | 1/2006 | Justin et al. ................. 623/20.3 |
| 2006/0069318 A1 | 3/2006 | Keaveny et al. ............. 600/300 |
| 2006/0111722 A1 | 5/2006 | Bouadi ............................. 606/79 |
| 2006/0111726 A1 | 5/2006 | Felt et al. ........................ 606/86 |
| 2006/0129246 A1 | 6/2006 | Steffensmeier ............ 623/20.29 |
| 2006/0136058 A1 | 6/2006 | Pietrzak ....................... 623/13.14 |
| 2006/0149374 A1 | 7/2006 | Winslow et al. ............. 623/17.11 |
| 2006/0190086 A1 | 8/2006 | Clemow et al. ............ 623/20.15 |
| 2006/0210017 A1 | 9/2006 | Lang ................................ 378/54 |
| 2006/0210018 A1 | 9/2006 | Lang ................................ 378/54 |
| 2006/0241776 A1 | 10/2006 | Brown et al. ............... 623/20.16 |
| 2006/0265078 A1 | 11/2006 | McMinn ..................... 623/20.14 |

(56) References Cited

U.S. PATENT DOCUMENTS

| | | | |
|---|---|---|---|
| 2007/0005143 A1 | 1/2007 | Ek et al. | 623/20.32 |
| 2007/0015995 A1 | 1/2007 | Lang | 600/407 |
| 2007/0047794 A1 | 3/2007 | Lang et al. | 378/132 |
| 2007/0067032 A1 | 3/2007 | Felt et al. | 623/14.12 |
| 2007/0083266 A1 | 4/2007 | Lang | 623/17.11 |
| 2007/0100462 A1 | 5/2007 | Lang et al. | 623/20.29 |
| 2007/0118055 A1 | 5/2007 | McCombs | 600/587 |
| 2007/0118222 A1 | 5/2007 | Lang | 623/17.12 |
| 2007/0118243 A1 | 5/2007 | Schroeder et al. | 700/118 |
| 2007/0142914 A1 | 6/2007 | Jones et al. | 623/14.13 |
| 2007/0156171 A1 | 7/2007 | Lang et al. | 606/205 |
| 2007/0190108 A1 | 8/2007 | Datta et al. | 424/423 |
| 2007/0198022 A1 | 8/2007 | Lang et al. | 606/88 |
| 2007/0203430 A1 | 8/2007 | Lang et al. | 600/587 |
| 2007/0226986 A1 | 10/2007 | Park et al. | 29/592 |
| 2007/0233156 A1 | 10/2007 | Metzger | 606/130 |
| 2007/0233269 A1 | 10/2007 | Steines et al. | 623/20.21 |
| 2007/0239165 A1 | 10/2007 | Amirouche | 606/86 |
| 2007/0250169 A1 | 10/2007 | Lang | 623/17.12 |
| 2007/0255288 A1 | 11/2007 | Mahfouz et al. | 606/102 |
| 2007/0274444 A1 | 11/2007 | Lang | 378/54 |
| 2007/0276224 A1 | 11/2007 | Lang et al. | 600/410 |
| 2007/0276501 A1* | 11/2007 | Betz et al. | 623/17.16 |
| 2007/0282451 A1 | 12/2007 | Metzger et al. | 623/20.28 |
| 2008/0004709 A1 | 1/2008 | O'Neill et al. | 623/20.35 |
| 2008/0009950 A1 | 1/2008 | Richardson | 623/20.29 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0119938 A1 | 5/2008 | Oh | 623/20.14 |
| 2008/0119940 A1 | 5/2008 | Otto et al. | 623/20.31 |
| 2008/0147072 A1 | 6/2008 | Park et al. | 606/87 |
| 2008/0170659 A1 | 7/2008 | Lang et al. | 378/56 |
| 2008/0172125 A1 | 7/2008 | Ek | 623/14.12 |
| 2008/0195108 A1 | 8/2008 | Bhatnagar et al. | 606/87 |
| 2008/0195216 A1 | 8/2008 | Philipp | 623/18.11 |
| 2008/0208348 A1 | 8/2008 | Fitz | 623/19.14 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0255445 A1 | 10/2008 | Neubauer et al. | 600/416 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 623/17.16 |
| 2008/0281426 A1 | 11/2008 | Fitz et al. | 623/17.16 |
| 2008/0319448 A1 | 12/2008 | Lavallee et al. | 606/102 |
| 2009/0076371 A1 | 3/2009 | Lang et al. | 600/407 |
| 2009/0076508 A1 | 3/2009 | Weinans et al. | 606/62 |
| 2009/0118830 A1 | 5/2009 | Fell | 623/14.12 |
| 2009/0131941 A1 | 5/2009 | Park et al. | 606/87 |
| 2009/0149977 A1 | 6/2009 | Schendel | 700/98 |
| 2009/0222103 A1 | 9/2009 | Fitz et al. | 623/18.11 |
| 2009/0226068 A1 | 9/2009 | Fitz et al. | 382/131 |
| 2009/0228111 A1 | 9/2009 | Otto | 623/20.19 |
| 2009/0228113 A1 | 9/2009 | Lang et al. | 623/20.32 |
| 2009/0270868 A1 | 10/2009 | Park et al. | 606/87 |
| 2009/0276045 A1 | 11/2009 | Lang | 623/14.12 |
| 2009/0306676 A1 | 12/2009 | Lang et al. | 606/102 |
| 2009/0312805 A1 | 12/2009 | Lang et al. | 606/86 R |
| 2009/0326666 A1 | 12/2009 | Wyss et al. | 623/20.39 |
| 2010/0054572 A1 | 3/2010 | Tsougarakis et al. | 382/131 |
| 2010/0217270 A1 | 8/2010 | Polinski et al. | 606/87 |
| 2010/0274534 A1 | 10/2010 | Steines et al. | 703/1 |
| 2010/0303313 A1 | 12/2010 | Lang et al. | 382/128 |
| 2010/0303317 A1 | 12/2010 | Tsougarakis et al. | 382/128 |
| 2010/0303324 A1 | 12/2010 | Lang et al. | 382/131 |
| 2010/0305708 A1 | 12/2010 | Lang et al. | 623/20.18 |
| 2010/0305907 A1 | 12/2010 | Fitz et al. | 703/1 |
| 2010/0329530 A1 | 12/2010 | Lang et al. | 382/131 |
| 2010/0331991 A1 | 12/2010 | Wilkinson et al. | 623/20.32 |
| 2011/0022179 A1 | 1/2011 | Andriacchi et al. | 623/20.18 |
| 2011/0029091 A1 | 2/2011 | Bojarski et al. | 623/20.32 |
| 2011/0029093 A1 | 2/2011 | Bojarski et al. | 623/20.35 |
| 2011/0046735 A1 | 2/2011 | Metzger et al. | 623/14.12 |
| 2011/0066245 A1 | 3/2011 | Lang et al. | 623/18.11 |
| 2011/0071645 A1 | 3/2011 | Bojarski et al. | 623/20.35 |
| 2011/0071802 A1 | 3/2011 | Bojarski et al. | 703/1 |
| 2011/0087332 A1 | 4/2011 | Bojarski et al. | 623/20.32 |
| 2011/0087465 A1 | 4/2011 | Mahfouz | 703/1 |
| 2011/0092804 A1 | 4/2011 | Schoenefeld et al. | 600/416 |
| 2011/0125009 A1 | 5/2011 | Lang et al. | 600/425 |
| 2011/0144760 A1 | 6/2011 | Wong et al. | 623/20.14 |
| 2011/0218635 A1 | 9/2011 | Amis et al. | 623/20.18 |
| 2011/0264097 A1 | 10/2011 | Hodorek et al. | 606/88 |
| 2011/0266265 A1 | 11/2011 | Lang | 219/121.72 |
| 2011/0288669 A1 | 11/2011 | Sanford et al. | 700/103 |
| 2011/0295378 A1 | 12/2011 | Bojarski et al. | 623/20.35 |
| 2011/0305379 A1 | 12/2011 | Mahfouz | 382/131 |
| 2012/0022659 A1 | 1/2012 | Wentorf | 623/20.32 |
| 2012/0093377 A1 | 4/2012 | Tsougarakis et al. | 382/128 |
| 2012/0116203 A1 | 5/2012 | Vancraen et al. | 600/407 |
| 2012/0191205 A1 | 7/2012 | Bojarski et al. | 623/20.32 |
| 2012/0191420 A1 | 7/2012 | Bojarski et al. | 703/1 |
| 2012/0197408 A1 | 8/2012 | Lang et al. | 623/18.11 |
| 2012/0201440 A1 | 8/2012 | Steines et al. | 382/131 |
| 2012/0209394 A1 | 8/2012 | Bojarski et al. | 623/20.32 |
| 2012/0232669 A1 | 9/2012 | Bojarski et al. | 623/20.3 |
| 2012/0232670 A1 | 9/2012 | Bojarski et al. | 623/20.35 |
| 2012/0232671 A1 | 9/2012 | Bojarski et al. | 623/20.35 |
| 2012/0265496 A1 | 10/2012 | Mahfouz | 703/1 |
| 2013/0006598 A1 | 1/2013 | Alexander et al. | 703/11 |
| 2013/0035766 A1 | 2/2013 | Meridew | 623/22.21 |
| 2013/0071828 A1 | 3/2013 | Lang et al. | 434/274 |
| 2013/0103363 A1 | 4/2013 | Lang et al. | 703/1 |
| 2013/0110471 A1 | 5/2013 | Lang et al. | 703/1 |
| 2013/0144570 A1 | 6/2013 | Axelson, Jr. et al. | 703/1 |
| 2013/0158671 A1 | 6/2013 | Uthgenannt et al. | 623/20.35 |
| 2013/0165939 A1 | 6/2013 | Ries et al. | 606/88 |
| 2013/0197870 A1 | 8/2013 | Steines et al. | 703/1 |
| 2013/0199259 A1 | 8/2013 | Smith | 72/362 |
| 2013/0203031 A1 | 8/2013 | Mckinnon et al. | 434/262 |
| 2013/0211531 A1 | 8/2013 | Steines et al. | 623/20.35 |
| 2013/0245803 A1 | 9/2013 | Lang | 700/98 |
| 2013/0297031 A1 | 11/2013 | Hafez | 623/20.14 |
| 2014/0005792 A1 | 1/2014 | Lang et al. | 623/20.32 |
| 2014/0029814 A1 | 1/2014 | Fitz et al. | 382/128 |
| 2014/0039631 A1 | 2/2014 | Bojarski et al. | 623/18.11 |
| 2014/0086780 A1 | 3/2014 | Miller et al. | 419/1 |
| 2014/0115872 A1 | 5/2014 | Steines et al. | 29/592 |
| 2014/0153798 A1 | 6/2014 | Tsougarakis et al. | 382/128 |
| 2014/0172111 A1 | 6/2014 | Lang et al. | 623/20.32 |
| 2014/0194996 A1 | 7/2014 | Bojarski et al. | 623/20.35 |
| 2014/0250677 A1 | 9/2014 | Lang | 29/592 |

FOREIGN PATENT DOCUMENTS

| | | | |
|---|---|---|---|
| CN | 101288597 | 10/2008 | A61B 17/56 |
| DE | 2306552 | 8/1974 | A61F 1/00 |
| DE | 3516743 | 11/1986 | A61F 2/36 |
| DE | 8909091 | 9/1989 | A61F 2/35 |
| DE | 3933459 | 4/1991 | A61F 2/00 |
| DE | 44 34 539 | 4/1996 | A61F 2/38 |
| DE | 19803673 | 8/1999 | A61L 27/54 |
| DE | 19926083 | 12/2000 | A61L 27/54 |
| DE | 10055465 | 5/2002 | A61L 24/00 |
| DE | 10135771 | 2/2003 | A61B 17/70 |
| DE | 102006037067 | 2/2008 | C04B 41/87 |
| EP | 0528080 | 2/1993 | A61F 2/30 |
| EP | 0600806 | 6/1994 | A61L 25/00 |
| EP | 0672397 | 9/1995 | A61F 2/38 |
| EP | 0 704 193 | 4/1996 | A61F 2/38 |
| EP | 0626156 | 7/1997 | A61F 2/38 |
| EP | 0613380 | 12/1999 | A61L 27/00 |
| EP | 1074229 | 2/2001 | A61F 2/38 |
| EP | 1077253 | 2/2001 | C12N 5/00 |
| EP | 1120087 | 8/2001 | A61B 17/06 |
| EP | 1129675 | 9/2001 | A61F 2/30 |
| EP | 0732091 | 12/2001 | A61F 2/38 |
| EP | 0896825 | 7/2002 | A61L 27/00 |
| EP | 0814731 | 8/2002 | A61F 2/30 |
| EP | 1234552 | 8/2002 | A61F 2/00 |

(56) References Cited

FOREIGN PATENT DOCUMENTS

| | | | |
|---|---|---|---|
| EP | 1234555 | 8/2002 | A61F 2/30 |
| EP | 0809987 | 10/2002 | A61F 2/38 |
| EP | 0833620 | 10/2002 | A61K 9/22 |
| EP | 1327423 | 7/2003 | A61F 2/38 |
| EP | 1329205 | 7/2003 | A61F 2/38 |
| EP | 0530804 | 6/2004 | A61L 25/00 |
| EP | 1437101 | 7/2004 | A61F 2/08 |
| EP | 1070487 | 9/2005 | A61F 2/08 |
| EP | 1683593 | 7/2006 | B22F 3/105 |
| EP | 1754457 | 2/2007 | A61F 2/38 |
| EP | 1886640 | 2/2008 | A61B 19/00 |
| EP | 2324799 | 5/2011 | A61F 2/38 |
| EP | 2173260 | 1/2012 | A61B 17/15 |
| FR | 2589720 | 11/1985 | A61F 2/38 |
| FR | 2740326 | 4/1997 | A61F 2/38 |
| GB | 1451283 | 9/1976 | A61F 1/24 |
| GB | 2291355 | 1/1996 | A61F 2/38 |
| GB | 2304051 | 3/1997 | A61F 2/38 |
| GB | 2348373 | 10/2000 | A61F 2/38 |
| JP | 56-083343 | 7/1981 | A61F 1/03 |
| JP | 61-247448 | 11/1986 | A61F 2/30 |
| JP | 1-249049 | 10/1989 | A61F 2/38 |
| JP | 05-184612 | 7/1993 | A61F 2/30 |
| JP | 7-236648 | 9/1995 | A61F 2/28 |
| JP | 8-25487 | 1/1996 | B29C 67/00 |
| JP | 8-173465 | 7/1996 | A61F 2/38 |
| JP | 9-169056 A | 6/1997 | B29C 67/00 |
| JP | 9-206322 | 8/1997 | A61F 2/36 |
| JP | 11-19104 | 1/1999 | A61F 2/28 |
| JP | 11-276510 | 10/1999 | A61F 2/28 |
| JP | 2004-166802 A | 6/2004 | A61F 2/38 |
| JP | 2005-532089 | 10/2005 | A61F 2/38 |
| JP | 2007-521881 | 8/2007 | A61F 2/44 |
| JP | 2007-236926 A | 9/2007 | A61F 2/36 |
| JP | 2010-538882 A | 12/2010 | B29C 67/00 |
| WO | WO 87/02882 | 5/1987 | A61F 2/38 |
| WO | WO 90/09769 | 9/1990 | A61F 2/28 |
| WO | WO 92/03108 | 3/1992 | A61F 2/38 |
| WO | WO 93/04710 | 3/1993 | A61L 25/00 |
| WO | WO 93/09819 | 5/1993 | A61L 27/00 |
| WO | WO 93/25157 | 12/1993 | A61B 17/56 |
| WO | WO 95/27450 | 10/1995 | A61F 2/38 |
| WO | WO 95/28688 | 10/1995 | G06T 15/00 |
| WO | WO 95/30390 | 11/1995 | A61F 2/38 |
| WO | WO 95/32623 | 12/1995 | A01N 1/02 |
| WO | WO 96/24302 | 8/1996 | A61B 17/90 |
| WO | WO 97/25942 | 7/1997 | A61F 2/32 |
| WO | WO 97/27885 | 8/1997 | A61L 27/00 |
| WO | WO 97/29703 | 8/1997 | A61B 17/56 |
| WO | WO 97/38676 | 10/1997 | A61K 9/10 |
| WO | WO 97/46665 | 12/1997 | C12N 5/06 |
| WO | WO 98/08469 | 3/1998 | A61F 2/30 |
| WO | WO 98/12994 | 4/1998 | A61F 2/28 |
| WO | WO 98/20816 | 5/1998 | A61F 2/38 |
| WO | WO 98/30617 | 7/1998 | C08G 63/12 |
| WO | WO 98/52498 | 11/1998 | A61F 2/28 |
| WO | WO 99/02654 | 1/1999 | C12N 5/00 |
| WO | WO 99/08598 | 2/1999 | A61B 8/00 |
| WO | WO 99/08728 | 2/1999 | A61L 27/00 |
| WO | WO 99/42061 | 8/1999 | A61F 2/38 |
| WO | WO 99/47186 | 9/1999 | A61L 27/00 |
| WO | WO 99/51719 | 10/1999 | C12M 3/00 |
| WO | WO 00/09179 | 2/2000 | A61L 25/00 |
| WO | WO 00/15153 | 3/2000 | A61F 2/38 |
| WO | WO 00/19911 | 4/2000 | A61B 17/02 |
| WO | WO 00/35346 | 6/2000 | A61B 5/11 |
| WO | WO 00/48550 | 8/2000 | |
| WO | WO 00/59411 | 10/2000 | A61F 2/38 |
| WO | WO 00/68749 | 11/2000 | G05B 19/4099 |
| WO | WO 00/74554 | 12/2000 | |
| WO | WO 00/74741 | 12/2000 | A61L 27/00 |
| WO | WO 00/76428 | 12/2000 | A61F 2/38 |
| WO | WO 01/10356 | 2/2001 | A61F 2/46 |
| WO | WO 01/17463 | 3/2001 | A61F 2/30 |
| WO | WO 01/19254 | 3/2001 | A61B 17/00 |
| WO | WO 01/35968 | 5/2001 | A61K 35/00 |
| WO | WO 01/45764 | 6/2001 | A61L 27/36 |
| WO | WO 01/68800 | 9/2001 | C12M 3/00 |
| WO | WO 01/70142 | 9/2001 | A61F 2/38 |
| WO | WO 01/77988 | 10/2001 | G06F 19/00 |
| WO | WO 01/82677 | 11/2001 | |
| WO | WO 01/91672 | 12/2001 | A61F 2/36 |
| WO | WO 02/02021 | 1/2002 | A61B 17/56 |
| WO | WO 02/09623 | 2/2002 | A61F 2/38 |
| WO | WO 02/22013 | 3/2002 | A61B 5/55 |
| WO | WO 02/22014 | 3/2002 | A61B 5/55 |
| WO | WO 02/23483 | 3/2002 | A61B 5/55 |
| WO | WO 02/34310 | 5/2002 | A61L 31/04 |
| WO | WO 02/36147 | 5/2002 | A61K 31/04 |
| WO | WO 02/37423 | 5/2002 | G06T 17/00 |
| WO | WO 02/061688 | 8/2002 | G06T 17/00 |
| WO | WO 02/096268 | 12/2002 | |
| WO | WO 03/007788 | 1/2003 | |
| WO | WO 03/013373 | 2/2003 | A61B 17/17 |
| WO | WO 03/037192 | 5/2003 | A61B 17/15 |
| WO | WO 03/047470 | 6/2003 | A61F 2/34 |
| WO | WO 03/051210 | 6/2003 | A61B 17/58 |
| WO | WO 03/061522 | 7/2003 | |
| WO | WO 03/094782 | 11/2003 | A61F 2/00 |
| WO | WO 03/099106 | 12/2003 | |
| WO | WO 2004/006811 | 1/2004 | A61F 2/46 |
| WO | WO 2004/032806 | 4/2004 | A61F 2/30 |
| WO | WO 2004/043305 | 5/2004 | A61F 2/30 |
| WO | WO 2004/047688 | 6/2004 | A61F 2/30 |
| WO | WO 2004/049981 | 6/2004 | A61F 2/46 |
| WO | WO 2004/051301 | 6/2004 | G01R 33/56 |
| WO | WO 2004/073550 | 9/2004 | |
| WO | WO 2005/002473 | 1/2005 | A61F 2/38 |
| WO | WO 2005/016175 | 2/2005 | |
| WO | WO 2005/020850 | 3/2005 | |
| WO | WO 2005/051239 | 6/2005 | A61F 2/08 |
| WO | WO 2005/051240 | 6/2005 | A61F 2/08 |
| WO | WO 2005/067521 | 7/2005 | |
| WO | WO 2005/076974 | 8/2005 | |
| WO | WO 2006/012370 | 2/2006 | B65D 45/04 |
| WO | WO 2006/058057 | 6/2006 | A61F 2/38 |
| WO | WO 2006/060795 | 6/2006 | A61B 17/17 |
| WO | WO 2006/065774 | 6/2006 | A61F 2/44 |
| WO | WO 2006/092600 | 9/2006 | A61B 19/00 |
| WO | WO 2007/041375 | 4/2007 | A61F 2/38 |
| WO | WO 2007/062079 | 5/2007 | A61F 2/30 |
| WO | WO 2007/092841 | 8/2007 | A61B 17/15 |
| WO | WO 2007/106172 | 9/2007 | A61F 2/38 |
| WO | WO 2007/109641 | 9/2007 | A61F 2/30 |
| WO | WO 2008/021494 | 2/2008 | G06F 19/00 |
| WO | WO 2008/055161 | 5/2008 | A61F 2/44 |
| WO | WO 2008/101090 | 8/2008 | A61F 2/38 |
| WO | WO 2008/117028 | 10/2008 | A61B 17/15 |
| WO | WO 2008/157412 | 12/2008 | A61B 17/17 |
| WO | WO 2009/039159 A2 | 3/2009 | B29C 67/00 |
| WO | WO 2009/068892 | 6/2009 | A61C 9/00 |
| WO | WO 2009/140294 | 11/2009 | A61F 2/30 |
| WO | WO 2010/099231 | 9/2010 | A61B 2/38 |
| WO | WO 2010/099353 | 9/2010 | A61F 2/30 |
| WO | WO 2010/099359 | 9/2010 | A61F 2/00 |
| WO | WO 2010/140036 | 12/2010 | A61F 2/38 |
| WO | WO 2010/151564 | 12/2010 | A61F 2/38 |
| WO | WO 2011/028624 | 3/2011 | A61F 2/38 |
| WO | WO 2011/056995 | 5/2011 | A61F 2/38 |
| WO | WO 2011/072235 | 6/2011 | A61F 2/38 |
| WO | WO 2011/075697 | 6/2011 | A61F 2/46 |
| WO | WO 2011/101474 | 8/2011 | G06F 19/00 |
| WO | WO 2012/027150 | 3/2012 | G06F 19/00 |
| WO | WO 2012/027185 | 3/2012 | G06T 17/00 |
| WO | WO 2012/112694 | 8/2012 | A61B 6/00 |
| WO | WO 2012/112698 | 8/2012 | A61F 2/30 |
| WO | WO 2012/112701 | 8/2012 | A61F 2/30 |
| WO | WO 2012/112702 | 8/2012 | A61F 2/30 |
| WO | WO 2013/020026 | 2/2013 | A61F 2/30 |
| WO | WO 2013/025814 | 2/2013 | A61F 2/38 |
| WO | WO 2013/056036 | 4/2013 | A61F 2/38 |
| WO | WO 2013/131066 | 9/2013 | A61F 2/38 |

(56) References Cited

FOREIGN PATENT DOCUMENTS

| WO | WO 2013/152341 | 10/2013 | ............... A61F 2/38 |
| WO | WO 2013/155500 | 10/2013 | ............... A61F 2/38 |
| WO | WO 2014/035991 | 3/2014 | ............. A61B 17/56 |

OTHER PUBLICATIONS

Adam et al., "MR Imaging of the Knee: Three-Dimensional Volume Imaging Combined with Fast Processing," J. Compt. Asst. Tomogr., 13(6): 984-988 (1989).
Adams et al., "Quantitative Imaging of Osteoarthritis," Semin Arthritis Rheum, 20(6) Suppl. 2: 26-39 (Jun. 1991).
Ahmad et al., "Biomechanical and Topographic Considerations for Autologous Osteochondral Grafting in the Knee," Am J Sports Med, 29(2): 201-206 (Mar.-Apr. 2001).
Alexander, "Estimating the motion of bones from markers on the skin," University of Illinois at Chicago (Doctoral Dissertation) (1998).
Alexander et al., "Correcting for deformation in skin-based marker systems," Proceedings of the 3rd Annual Gait and Clinical Movement Analysis Meeting, San Diego, CA (1998).
Alexander et al., "Internal to external correspondence in the analysis of lower limb bone motion," Proceedings of the 1999 ASME Summer Bioengineering Conference, Big Sky, Montana (1999).
Alexander et al., "State estimation theory in human movement analysis," Proceedings of the ASME International Mechanical Engineering Congress (1998).
Alexander et al., "Optimization techniques for skin deformation correction," International Symposium on 3-D Human Movement Conference, Chattanooga, TN, (1998).
Alexander et al., "Dynamic Functional Imaging of the Musculoskeletal System," ASME Winter International Congress and Exposition, Nashville, TN (1999).
Allen et al., "Late degenerative changes after meniscectomy 5 factors affecting the knee after operations," J Bone Joint Surg 66B: 666-671 (1984).
Alley et al., "Ultrafast contrast-enhanced three dimensional MR Aagiography: State of the art," Radiographics 18: 273-285 (1998).
Andersson et al., "MacIntosh Arthroplasty in Rheumatoid Arthritis," Acta. Orthrop. Scand. 45(2):245-259 (1974).
Andriacchi, "Dynamics of knee Malalignment," Orthop Clin North Am 25: 395-403 (1994).
Andriacchi, et al., "A point cluster method for in vivo motion analysis: Applied to a study of knee kinematics," J. Biomech Eng 120(12): 743-749 (1998).
Andriacchi, et al., "Methods for evaluating the progression of Osterarthiritis," Journal of Rehabilitation Research and Development 37(2): 163-170 (2000).
Andriacchi et al., "Gait analysis as a tool to assess joint kinetics biomechanics of normal and pathological human articulating joints," Nijhoff, Series E 93: 83-102 (1985).
Andriacchi et al., "In vivo measurement of six-degrees-of-freedom knee movement during functional testing," Transactions of the Orthopedic Research Society 698 (1995).
Argenson et al., "Is There a Place for Patellofemoral Arthroplasty?," Clinical Orthopaedics and Related Research No. 321, pp. 162-167 (1995).
Aro et al., "Clinical Use of Bone Allografts," Ann Med 25:403-412 (1993).
Bashir, "Validation of Gadolinium-Enhanced MRI of FAF Measurement in Human Cartilage," Intl. Soc. Mag. Resonance Med. (1998).
Beaulieu et al., "Glenohumeral relationships during physiological shoulder motion and stress testing: Initial experience with open MRI and active Scan-25 plane registration," Radiology (1999).
Beaulieu et al., "Dynamic imaging of glenohumeral instability with open MRI," Int. Society for Magnetic Resonance in Medicine Sydney, Australia (1998).

Beckmann et al., "Noninvasive 3D MR Microscopy as Tool in Pharmacological Research: Application to a Model of Rheumatoid Arthritis," Magn Reson Imaging 13(7): 1013-1017 (1995).
Billet, Philippe, French Version—"Gliding Knee Prostheses—Analysis of Mechanical Failures", Thesis, Medical School of Marseilles, 1982, 64 pages.
Billet, Philippe, Translated Version—"Gliding Knee Prostheses—Analysis of Mechanical Failures", Thesis, Medical School of Marseilles, 1982, 93 pages.
Blazina et al., "Patellofemoral replacement: Utilizing a customized femoral groove replacement," 5(1)53-55 (1990).
Blum et al., "Knee Arthroplasty in Patients with Rheumatoid Arthritis," ANN. Rheum. Dis. 33 (1): 1-11 (1974).
Bobic, "Arthroscopic osteochondral autogaft transplantation in anterior cruciate ligament reconstruction: a preliminary clinical study," Knee Surg Sports Traumatol Arthrosc 3(4): 262-264 (1996).
Boe et al., "Arthroscopic partial meniscectomy in patients aged over 50," J. Bone Joint Surg 68B: 707 (1986).
Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).
Borthakur et al., "In Vivo Triple Quantum Filtered Sodium MRI of Human Articular Cartilage," Proc. Intl. Soc. Mag. Resonance Med., 7:549 (1999).
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
Bregler et al., "Recovering non-rigid 3D shape from image streams," Proc. IEEE Conference on Computer Vision and Pattern Recognition (Jun. 2000).
Brett et al., "Quantitative Analysis of Biomedical Images," Univ. of Manchester, Zeneca Pharmaceuticals, IBM UK, http://www.wiau.man.ac.uk/~ads/imv (1998).
Brittberg et al., "A critical analysis of cartilage repair," Acta Orthop Scand 68(2): 186-191 (1997).
Brittberg et al., "Treatment of deep cartilage defects in the knee with autologous chrondrocyte transplantation," N Engl J Med 331(14): 889-895 (1994).
Broderick et al., "Severity of articular cartilage abnormality in patients with osteoarthritis: evaluation with fast spin-echo MR vs. arthroscopy," AJR 162: 99-103 (1994).
Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al., "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).
Butts et al., "Real-Time MR imaging of joint motion on an open MR imaging scanner," Radiological Society of North America, 83rd Scientific Assembly and Annual Meeting, Chicago, IL (1997).
Cameron, et al., "Review of a Failed Knee Replacement and Some Observations on the Design of a Knee Resurfacing Prosthesis," Arch. Orthop Trauma Surg. 97(2):87-89 (1980).
CAOS, "MIS meets CAOS Spring 2005 Symposium Schedule", *CAOS Spring 2005 Symposium*, pp. 1-9, May 19, 2005.
Carano et al., "Estimation of Erosive Changes in Rheumatoid Arthritis by Temporal Multispectral Analysis," Proc. Intl. Soc. Mag. Resonance Med., 7:408 (1999).
Carr et al., "Surface Interpolation with Radial Basis Functions for Medical Imaging," IEEE Transactions on Medical Imaging, IEEE, Inc. New York, vol. 16, pp. 96-107 (Feb. 1997).

(56) References Cited

OTHER PUBLICATIONS

Castriota-Scanderbeg et al., "Precision of Sonographic Measurement of Articular Cartilage: Inter-and Intraobserver Analysis," Skeletal Radiol 25: 545-549 (1996).
Chan et al., "Osteoarthritis of the Knee: Comparison of Radiography, CT and MR Imaging to Asses Extent and Severity," AJR Am J Roentgenol 157(4): 799-806 (1991).
Chelule et al., "Patient-Specific Template to Preserve Bone Stock in Total Knee Replacement: Preliminary Results", *15th Annual ISTA Symposium*, Sep. 2002, 1 page.
Clarke et al., "Human Hip Joint Geometry and Hemiarthroplasty Selection," The Hip. C.V. Mosby, St. Louis 63-89 (1975).
Clary et al., "Experience with the MacIntosh Knee Prosthesis," South Med. J. 65(3):265-272 (1972).
Cohen et al., "Knee cartilage topography, thickness, and contact areas from MRI: in-vitro calibration and in-vivo measurements," Osteoarthritis and Cartilage 7: 95-109 (1999).
Cohen et al., "Computer-Aided Planning of Patellofemoral Joint OA Surgery: Developing Physical Models from Patient MRI", MICCAI, Oct. 11-13, 1998, 13 pages.
Conaty, et al., "Surgery of the Hip and Knee in Patients with Rheumatoid Arthritis," J. Bone Joint Surg. Am. 55(2):301-314 (1973).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).
Dardzinski et al., "Entropy Mapping of Articular Cartilage", ISMRM Seventh Scientific Meeting, Philadelphia, PA (1999) T. 41, V. II.
Dardzinski et al., "T1-T2 Comparison in Adult Articular Cartilage," ISMRM Seventh Scientific Meeting, Philadelphia, PA (May 22-28, 1999).
De Winter et al., "The Richards Type II Patellofemoral Arthroplasty", Acta Orthop Scand 2001; 72 (5): 487-490.
Delp et al., "A Graphics-Based Software System to Develop and Analyze Models of Musculoskeletal Structures," Comput. Biol. Med., vol. 25, No. 1, pp. 21-34, 1995.
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Doherty et al., Osteoarthritis, Oxford Textbook of Rheumatology, Oxford University Press 959-983 (1993).
Dougados et al., "Longitudinal radiologic evaluation of osteoarthritis of the knee," J Rheumatol 19: 378-384 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).

Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient and Section Orientation on Quantitative Analyses of Knee Joint Cartilage," Journal of Magnetic Resonance Imaging 11: 161-167 (2000).
Eckstein et al., "Effect of Physical Exercise on Cartilage Volume and Thickness In Vivo: An MR Imaging Study," Radiology 207: 243-248 (1998).
Eckstein et al., "Functional Analysis of Articular Cartilage Deformation, Recovery, and Fluid Flow Following Dynamic Exercise In Vivo," Anatomy and Embryology 200: 419-424 (1999).
Eckstein et al., "In Vivo Reproducibility of Three-Dimensional Cartilage Volume and Thickness Measurements With MR Imaging", AJR 170(3): 593-597 (1998).
Eckstein et al., "New Quantitative Approaches With 3-D MRI: Cartilage Morphology, Function and Degeneration", Medical Imaging International, Nov.-Dec. 1998.
Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).
Eckstein et al., Accuracy of Cartilage Volume and Thickness Measurements with Magnetic Resonance Imaging, Clin. Orthop. 1998; 352: 137-148 T. 60 V. II.
Eckstein et al., "Magnetic Resonance Chondro-Crassometry (MR CCM): A Method for Accurate Determination of Articular Cartilage Thickness?" Magn. Reson. Med. 35: 89-96 (1996).
Eckstein et al., "The Influence of Geometry on the Stress Distribution in Joints—A Finite Element Analysis," Anat Embryol, 189: 545-552 (1994).
Eckstein et al., "The Morphology of Articular Cartilage Assessed by Magnetic Resonance Imaging: Reproducibility and Anatomical Correlation," Sur. Radiol Anat 16: 429-438 (1994).
Elting et al., "Unilateral frame distraction: proximal tibial valgus osteotomy for medial gonarthritis," Contemp Orthrop 27(6): 522-524 (1993).
Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).
Faber et al., "Quantitative Changes of Articular Cartilage Microstructure During Compression of an Intact Joint," Proc. Intl. Soc. Mag. Resonance Med., 7:547 (1999).
Falcao et al., "User-steered image segmentation paradigms. Live wire and live lane," Graphical Models and Image Processing 60: 233-260 (1998).
Felson et al., "Weight Loss Reduces the risk for symptomatic knee osteoarthritis in women: the Framingham study," Ann Intern Med 116: 535-539 (1992).
Gandy et al., "One-Year Longitudinal Study of Femoral Cartilage Lesions in Knee Arthritis," Proc. Intl. Soc. Mag. Resonance Med., 7:1032 (1999).
Garrett, "Osteochondral allografts for reconstruction of articular defects of the knee," Instr Course Lect 47: 517-522 (1998).
Gerscovich, "A Radiologist's Guide to the Imaging in the Diagnosis and Treatment of Developmental Dysplasia of the Hip," Skeletal Radiol 26: 447-456 (1997).
Ghelman et al., "Kinematics of the Knee After Prosthetic Replacements", Clin. Orthop. May 1975: (108): 149-157.
Ghosh et al., "Watershed Segmentation of High Resolution Articular Cartilage Images for Assessment of Osteoarthritis," International Society for Magnetic Resonance in Medicine, Philadelphia, (1999).
Glaser et al., "Optimization and Validation of a Rapid Highresolution T1-W 3-D Flash Waterexcitation MR Sequence for the Quantitative Assessment of Articular Cartilage Volume and Thickness," Magnetic Resonance Imaging 19: 177-185 (2001).
Goodwin et al., "MR Imaging of Articular Cartilage: Striations in the Radial Layer Reflect the Fibrous Structure of Cartilage," Proc. Intl. Soc. Mag. Resonance Med., 7:546 (1999).
Gouraud, "Continuous shading of curved surfaces," IEEE Trans on Computers C-20(6) (1971).

(56) References Cited

OTHER PUBLICATIONS

Graichen et al., "Three-Dimensional Analysis of the Width of the Subacromial Space in Healthy Subjects and Patients With Impingement Syndrome," American Journal of Roentgenology 172: 1081-1086 (1999).
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).
Hardy et al., "Measuring the Thickness of Articular Cartilage From MR Images," J. Magnetic Resonance Imaging 13: 120-126 (2001).
Hardy et al., "The Influence of the Resolution and Contrast on Measuring the Articular Cartilage Volume in Magnetic Resonance Images" Magn Reson Imaging. 18(8): 965-972 (Oct. 2000).
Hargreaves et al., "MR Imaging of Articular Cartilage Using Driven Equilibrium," Magnetic Resonance in Medicine 42(4): 695-703 (Oct. 1999).
Hargreaves et al., "Technical considerations for DEFT imaging," International Society for Magnetic Resonance in Medicine, Sydney, Australia (Apr. 17-24, 1998).
Hargreaves et al., "Imaging of articular cartilage using driven equilibrium," International Society for Magnetic Resonance in Medicine, Sydney, Australia (Apr. 17-24, 1998).
Harryson et al., "Custom-Designed Orthopedic Implants Evaluated Using Finite Element Analysis of Patient-Specific Computed Tomoraphy Data: Femoral-Component Case Study", BMC Musculoskeletal Disorders, vol. 8(91), Sep. 2007, 10 pages.
Hastings et al., "Double Hemiarthroplasty of the Knee in Rheumatoid Arthritis," A Survey of Fifty Consecutive Cases, J. Bone Joint Surg. Br. 55(1):112-118 (1973).
Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).
Haut et al., "A High Accuracy Three-Dimensional Coordinate Digitizing System for Reconstructing the Geometry of Diarthrodial Joints," J. Biomechanics 31: 571-577 (1998).
Hayes et al., "Evaluation of Articular Cartilage: Radiographic and Cross-Sectional Imaging Techniques," Radiographics 12: 409-428 (1992).
Henderson et al., "Experience with the Use of the Macintosh Prosthesis in Knees of Patients with Pheumatoid Arthritis," South. Med. J. 62(11):1311-1315 (1969).
Henkelman, "Anisotropy of NMR Properties of Tissues", Magn Res Med. 32: 592-601 (1994).
Herberhold et al., "An MR-Based Technique for Quantifying the Deformation of Articular Cartilage During Mechanical Loading in an Intact Cadaver Joint," Magnetic Resonance in Medicine 39(5): 843-850 (1998).
Herberhold, "In Situ Measurement of Articular Cartilage Deformation In Intact Femorapatellar Joints Under Static Loading", Journal of biomechanics 32: 1287-1295 (1999).
Herrmann et al., "High Resolution Imaging of Normal and Osteoarthritic Cartilage with Optical Coherence Tomogrqaphy," J. Rheumatoil 26: 627-635 (1999).
High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).
Hohe, "Surface Size, Curvature Analysis, and Assessment of Knee Joint Incongruity With MR Imaging In Vivo", Magnetic Resonance in Medicine, 47: 554-561 (2002).
Holdsworth et al., "Benefits of Articular Cartilage Imaging at 4 Tesla: An In Vivo Study of Normal Volunteers," Proc. Intl. Soc. Mag. Resonance Med., 7:1028 (1999).
Hughes et al., "Technical Note: A Technique for Measuring the Surface Area of Articular Cartilage in Acetabular Fractures," Br. J. Radiol; 67: 584-588 (1994).
Husmann et al., "Three-Dimensional Morphology of the Proximal Femur," J. Arthroplasty; 12(4): 444-450 (Jun. 1997).
Hyhlik-Durr et al., "Precision of Tibial Cartilage Morphometry with a coronal water-excitation MR sequence," European Radiology 10(2): 297-303 (2000).
Ihara H., "Double-Contrast CT Arthrography of the Cartilage of the Patellofemoral Joint," Clin. Orthop.; 198: 50-55 (Sep. 1985).
Iida et al., "Socket Location in Total Hip Replacement: Preoperative Computed Tomography and Computer Simulation" Acta Orthop Scand; 59(1): 1-5 (1998).
Irarrazabal et al., "Fast three-dimensional magnetic resonance imaging," Mag Res. Med. 33: 656-662 (1995).
Jessop et al., "Follow-up of the MacIntosh Arthroplasty of the Knee Joint," Rheumatol Phys. Med. 11(5):217-224 (1972).
Johnson et al., "The distribution of load across the knee. A comparison of static and dynamic measurements," J. Bone Joint Surg 62B: 346-349 (1980).
Johnson, "In vivo contact kinematics of the knee joint: Advancing the point cluster technique," Ph.D. Thesis, University of Minnesota (1999).
Johnson et al., "Development of a knee wear method based on prosthetic in vivo slip velocity," Transaction of the Orthopedic Research Society, 46th Annual Meeting (Mar. 2000).
Jonsson et al., "Precision of Hyaline Cartilage Thickness Measurements," Acta Radiol 1992; 33(3): 234-239 (1992).
Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).
Karvonen et al., "Articular Cartilage Defects of the Knee: Correlation Between Magnetic Resonance Imaging and Gross Pathology," Ann Rheum Dis. 49: 672-675 (1990).
Kass et al., "Snakes: Active contour models.," Int J Comput Vision 1: 321-331 (1988).
Kates, et al., "Experiences of Arthroplasty of the Rheumatoid Knee Using MacIntosh Prostheses," Ann. Rheum. Dis. 28(3):328 (1969).
Kaufman et al., "Articular Cartilage Sodium content as a function of compression" Seventh Scientific Meeting of ISMRM, p. 1022, 1999 T. 105, V. III.
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Klosterman et al., "T2 Measurements in Adult Patellar Cartilage at 1.5 and 3.0 Tesla," ISMRM Seventh Scientific Meeting, Philadelphia, PA, (May 22-28, 1999).
Knauss et al., "Self-Diffusion of Water in Cartilage and Cartilage Components as Studied by Pulsed Field Gradient NMR," Magnetic Resonance in Medicine 41:285-292 (1999).
Koh et al., "Visualization by Magnetic Resonance Imaging of Focal Cartilage Lesions in the Excised Mini-Pig Knee," J. Orthop. Res; 14(4): 554-561 (Jul. 1996).
Korhonen et al., "Importance of the Superficial Tissue Layer for the Indentation Stiffness of Articular Cartilage," Med. Eng. Phys; 24(2): 99-108 (Mar. 2002).
Korkala et al., "Autogenous Osteoperiosteal Grafts in the Reconstruction of Full-Thickness Joint Surface Defects," Int. Orthop.; 15(3): 233-237 (1991).
Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).
Kwak et al., "Anatomy of Human Patellofemoral Joint Articular Cartilage: Surface Curvature Analysis," J. Orthop. Res.; 15: 468-472 (1997).

(56) References Cited

OTHER PUBLICATIONS

LaFortune et al., "Three dimensional kinematics of the human knee during walking," J. Biomechanics 25: 347-357 (1992).
Lam et al., "X-Ray Diagnosis: A Physician's Approach", Editor Lam, 1998, Springer-Verlag publishers, Title page and Index Only (ISBN 9813083247).
Lang et al., "Functional joint imaging: a new technique integrating MRI and biomotion studies," International Society for Magnetic Resonance in Medicine, Denver (Apr. 18-24, 2000).
Lang et al., Risk factors for progression of cartilage loss: a longitudinal MRI study. European Society of Musculoskeletal Radiology, 6th Annual Meeting, Edinburgh, Scotland (1999).
Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).
Ledingham et al., "Factors affecting radiographic progression of knee osteoarthritis," Ann Rheum Dis 54: 53-58 (1995).
Leenslag et al., "A Porous Composite for Reconstruction of Meniscus Lesions," Biological and Biomechanical Perform. of Biomaterials, Elsevier Science Publishers Amsterdam pp. 147-152 (1986).
Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).
Li et al., A Boundary Optimization Algorithm for Delineating Brain Objects from CT Scans: Nuclear Science Symposium and Medical Imaging Conference 1993 IEEE Conference Record, San Francisco, CA (1993).
Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).
Lombardi, Jr. et al., "Patient-Specific Approach in Total Knee Arthroplasty", Orthopedics, vol. 31, Issue 9, Sep. 2008, 8 pages.
Lorensen et al., "Marching cubes: a high resolution 3d surface construction algorithm," Comput Graph 21: 163-169 (1987).
Losch et al., "A non-invasive technique for 3-dimensional assessment of articular cartilage thickness based on MRI part 1: development of a computational method," Magn Res Imaging 15(7): 795-804 (1997).
Lu et al., "Bone position estimation from skin marker co-ordinates using globals optimization with joint constraints," J Biomechanics 32: 129-134 (1999).
Lu et al., "In vitro degradation of porous poly(L-lactic acid) foams", Biomaterials, 21(15):1595-1605, Aug. 2000.
Lucchetti et al., "Skin movement artefact assessment and compensation in the estimation of knee-joint kinematics," J Biomechanics 31: 977-984 (1998).
Lusse et al., "Measurement of Distribution of Water Content of Human Articular Cartilage Based on Transverse Relaxation Times: An In Vitro Study," Seventh Scientific Meeting of ISMRM, p. 1020 (1999).
Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).
MacIntosh, "Arthroplasty of the Knee in Rheumatoid Arthritis," Proceedings and Reports of Councils and Assotions, J. Bone & Joint Surg., vol. 48B No. (1): 179 (Feb. 1966).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Maki et al., "SNR improvement in NMR microscopy using DEFT," J Mag Res; pp. 482-492 (1988).
Marler et al., "Soft-Tissue Augmentation with Injectable Alginate and Syngeneic Fibroblasts", Plastic & Reconstructive Surgery, 105(6):2049-2058, May 2000.
Marshall et al., "Quantitation of Articular Cartilage Using Magnetic Resonance Imaging and Three-Dimensional Reconstruction," J. Orthop. Res.; 13: 814-823 (1995).
Matsen, III et al., "Robotic Assistance in Orthopaedic Surgery: A Proof of Principle Using Distal Femoral Arthroplasty", Clinical Ortho. and Related Research, 296:178-186 (1993).
Mattila et al., "Massive Osteoarticular Knee Allografts: Structural Changes Evaluated with CT," Radiology; 196: 657-660 (1995).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Merkle et al., "A Transceiver Coil Assembly for Hetero-Nuclear Investigations of Human Breast at 4T," Proc. Intl. Soc. Mag. Resonance Med., 7:170 (1999).
Meyer et al., "Simultaneous spatial and spectral selective excitation," Magn Res Med 15: 287-304 (1990).
Mills et al., "Magnetic Resonance Imaging of the Knee: Evaluation of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life", Am. J. Orthop. Nov. 1998; 27: 739-744.
Modest et al., "Optical Verification of a Technique for In Situ Ultrasonic Measurement of Articular Cartilage Thickness," J. Biomechanics 22(2): 171-176 (1989).
Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).
Mumtaz et al., "Selective Laser Melting of Inconel 625 Using Pulse Shaping", Rapid Prototyping Journal, vol. 16, Iss. 4, pp. 248-257, 2010.
Mundinger et al., "Magnetic Resonance Tomography in the Diagnosis of Peripheral Joints," Schweiz Med. Wochenschr. 121(15): 517-527 (1991) (Abstract Only).
Myers et al., "Experimental Assessment by High Frequency Ultrasound of Articular Cartilage Thickness and Osteoarthritic Changes," J. Rheumatol; 22: 109-116 (1995).
Nelson et al., "Arthroplasty and Arthrodesis of the Knee Joint," Orthop. Clin. North Am. 2 (1): 245-64 (1971).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).
Nizard, "Role of tibial osteotomy in the treatment of medical femorotibial osteoarthritis," Rev Rhum Engl Ed 65(7-9): 443-446 (1998).
Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Overhoff et al., "Total Knee Arthroplasty: Coordinate System Definition and Planning Based on 3-D Ultrasound Image Volumes", CARS 2001, pp. 283-288.
Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).

(56) References Cited

OTHER PUBLICATIONS

Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the metacarpophalangeal joints of the hand: accuracy and precision of three-dimensional MR imaging," AJR 165: 371-375 (1995).
Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).
Peterfy et al., "Quantification of articular cartilage in the knee with pulsed saturation transfer subtraction and fat-suppressed MR imaging: optimization and validation," Radiology 192(2): 485-491 (1994).
Peterfy et al., "Emerging Applications of Magnetic Resonance Imaging in the Evaluation of Articular Cartilage," Radiol Clin North Am.; 34(2): 195-213 (Mar. 1996).
Petrovic et al., "Additive Manufacturing Solutions for Improved Medical Implants", Biomedicine, INTECH, pp. 148-180, Mar. 2012.
Pilch et al., "Assessment of Cartilage Volume in The Femorotibial Joint With Magnetic Resonance Imaging and 3D Computer Reconstruction," J. Rheumatol. 21(12): 2307-2319 (1994).
Piplani et al., "Articular cartilage volume in the knee: semi-automated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I—III, MRCAS '94, Pittsburgh, PA, pp. 42-48 (Sep. 22-24, 1994).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher et al., "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke Hw, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo FLASH MR imaging in the detection of patel-lofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028 (1999).
Robinson et al., "The Early Innovators of Today's Resurfacing Condylar Knees", The Journal of Arthroplasty, vol. 20, No. 1, Suppl. 1, 2005.
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an—dimensional digitized picture with applications," Pattern Recognition 27(11): 1551-1565 (1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schipplein et al., "Interaction between active and passive knee stabilizers during level walking," J Orthop Res 9: 113-119 (1991).

(56) References Cited

OTHER PUBLICATIONS

Schorn et al., "MacIntosh Arthroplasty in Rheumatoid Arthritis," Rheumatol Rehabil. Aug. 1978:17(3):155-163.
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 298-310 (1972).
Sittek et al., "Assessment of Normal Patellar Cartilage Volume and Thickness Using MRI: an Analysis of Currently Available Pulse Sequences", Skeletal Radiol 1996; 25: 55-61.
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Slone et al., "Body CT: A Practical Approach", Editor Slone, 1999 McGraw-Hill publishers, Title page and Table of Contents pgs. Only (ISBN 007058219).
Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).
Stammberger et al., "A Method for Quantifying Time Dependent Changes in MR Signal Intensity of Articular Cartilage as a Function of Tissue Deformation in Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).
Stammberger et al., "Elastic Registration of 3D Cartilage Surfaces From MR Image Data for Detecting Local Changes of the Cartilage Thickness," Magnetic Resonance in Medicine 44: 592-601 (2000).
Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Stauffer et al., "The MacIntosh Prosthesis. Prospective Clinical and Gait Evaluation," Arch. Surg. 110(6):717-720 (1975).
Steines et al., Segmentation of osteoarthritic femoral cartilage using live wire, Proc. Intl. Soc. Mag. Resonance Med., 8:220 (2000).
Steines et al., "Segmentation of osteoarthritis femoral cartilage from MR images," CARS—Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Stout et al., "X-Ray Structure Determination: A Practical Guide", $2^{nd}$ Ed. Editors Stout and Jensen, 1989, John Wiley & Sons, Title page and Table of Contents pgs. Only (ISBN 0471607118).

Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Tebben et al., "Three-Dimensional Computerized Reconstruction. Illustration of Incremental Articular Cartilage Thinning," Invest. Radiol. 32(8): 475-484 (1997).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).
Tsai et al., "Application of a flexible loop-gap resonator for MR imaging of articular cartilage at 3.TO," International Society for Magnetic Resonance in Medicine, Denver (Apr. 24-28, 2000) 8:2127.
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).
Vandeberg et al., "Assessment of Knee Cartilage in Cadavers with Dual-Detector Sprial CT ARthrography and MR Imaging", Radiology, Feb. 2002: 222(2): 430-435 T. 195, V.V.
Van der Linden et al., "MR Imaging of Hyaline Cartilage at 0.5 T: A Quantitative and Qualitative in vitro Evaluation of Three Types of Sequences" pp. 297-305 (Jun. 1998).
Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).

(56) References Cited

OTHER PUBLICATIONS

Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," ANN Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US03/38158, dated Feb. 23, 2005, 7 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/042421, dated May 18, 2006, together with the Written Opinion of the International Searching Authority, 7 pages.
European Patent Office, Supplementary European Search Report—Application No. 04812273.3, dated Oct. 8, 2007, 6 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Search Report—International Application No. PCT/US06/38212, dated Apr. 22, 2008, together with the Written Opinion of the International Searching Authority, 7 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
European Patent Office, European Search Report—International Application No. PCT/US2006/045131 dated Mar. 3, 2010, 6 pages.
International Searching Authority, International Search Report—International Application No. PCT/US2010/025459, dated Apr. 20, 2010, together with the Written Opinion of the International Searching Authority, 15 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
International Searching Authority, International Search Report—International Application No. PCT/US2010/025274, dated Sep. 20, 2010, together with the Written Opinion of the International Searching Authority, 18 pages.
International Searching Authority, International Search Report—International Application No. PCT/US2010/046868, dated Jan. 7, 2011, together with the Written Opinion of the International Searching Authority, 11 pages.
European Patent Office, Extended European Search Report—European Application No. 10012404.9-2310, dated Apr. 1, 2011, 7 pages.
International Searching Authority, International Search Report—International Application No. PCT/US2010/055483, dated Jul. 28, 2011, together with the Written Opinion of the International Searching Authority, 9 pages.
International Searching Authority, International Search Report—International Application No. PCT/US2010/059910 dated Oct. 25, 2011, together with the Written Opinion of the International Searching Authority, 9 pages.
International Searching Authority, International Search Report—International Application No. PCT/US2010/061141, dated Aug. 31, 2011, together with the Written Opinion of the International Searching Authority, 8 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2012/050964 dated Oct. 22, 2012, together with the Written Opinion of the International Searching Authority, 13 pages.
European Patent Office, European Search Report—Application No. 12170854.9-1526 dated Oct. 9, 2012, 6 pages.

(56) References Cited

OTHER PUBLICATIONS

International Searching Authority, International Search Report—International Application No. PCT/US12/59936 dated Jan. 9, 2013, together with the Written Opinion of the International Searching Authority, 11 pages.
European Patent Office, Extended European Search Report—Application No. 10792589.3-2310 dated Feb. 7, 2013, 9 pages.
European Patent Office, European Search Report—Application No. 10192339.9-1257 dated Jan. 23, 2013, 5 pages.
European Patent Office, Extended European Search Report—Application No. 10746859.7-1654 dated Mar. 4, 2013, 7 pages.
European Patent Office, Extended European Search Report—Application No. 12192903.8-1654 dated Apr. 17, 2013, 8 pages.
International Searching Authority, International Search Report—International Application No. PCT/US2012/025280, dated Oct. 25, 2012, together with the Written Opinion of the International Searching Authority, 11 pages.
International Searching Authority, International Search Report—International Application No. PCT/US2009/036165, dated May 7, 2009, together with the Written Opinion of the International Searching Authority, 9 pages.
International Searching Authority, International Search Report—International Application No. PCT/US2012/025274, dated Oct. 25, 2012, together with the Written Opinion of the International Searching Authority, 12 pages.
International Searching Authority, International Search Report—International Application No. PCT/US2012/025277, dated Oct. 25, 2012, together with the Written Opinion of the International Searching Authority, 12 pages.
European Patent Office, European Search Report—Application No. 10829105.5-1654 dated Nov. 5, 2013, 3 pages.
European Patent Office, Extended European Search Report—Application No. 10838327.4-1654 dated Nov. 14, 2013, 6 pages.
International Searching Authority, Great Britain Search and Examination Report—Application No. GB1201112.8 dated Feb. 3, 2014, 4 pages.
International Searching Authority, International Search Report—International Application No. PCT/US2013/035536 dated Jul. 18, 2013, together with the Written Opinion of the International Searching Authority, 9 pages.
International Searching Authority, International Search Report—International Application No. PCT/US2013/028762 dated Jun. 21, 2013, together with the Written Opinion of the International Searching Authority, 13 pages.
International Searching Authority, International Search Report—International Application No. PCT/US2013/061042 dated Jan. 10, 2014, together with the Written Opinion of the International Searching Authority, 12 pages.
International Searching Authority, International Search Report—International Application No. PCT/US13/56841 dated Feb. 12, 2014, together with the Written Opinion of the International Searching Authority, 9 pages.
European Patent Office, Extended European Search Report—Application No. 10836760.9-1654 dated Apr. 11, 2014, 6 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (U.S. Pat. No. 2004/0167390), 11 pages.

Bromberg & Sunstein LLP, Response to Office Action dated Jan. 9, 2009, pertaining to U.S. Appl. No. 10/764,010 (U.S. Pat. No. 2004/0167390), 25 pages.
United States Patent and Trademark Office, Office Action dated Oct. 23, 2009, pertaining to U.S. Appl. No. 10/764,010 (U.S. Pat. No. 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.
United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.

(56) References Cited

OTHER PUBLICATIONS

United States Patent and Trademark Office, Office Action dated Sep. 15, 2010, pertaining to U.S. Appl. No. 10/704,208, 13 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
United States Patent and Trademark Office, Office Action dated Feb. 22, 2011, pertaining to U.S. Appl. No. 11/602,713, 10 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
International Searching Authority, International Search Report—International Application No. PCT/US2008/05377, dated Sep. 30, 2008, together with the Written Opinion of the International Searching Authority, 17 pages.
International Searching Authority, International Search Report—International Application No. PCT/US2013/036505 dated Jul. 29, 2013, together with the Written Opinion of the International Searching Authority, 7 pages.
International Searching Authority, Invitation to Pay Additional Fees—International Application No. PCT/US2008/053977, dated Jul. 11, 2008, together with the Written Opinion of the International Searching Authority, 6 pages.
European Patent Office, Extended European Search Report—Application No. 13775348.9-1654 dated Mar. 10, 2015, 6 pages.
United States Patent & Trademark Office, Office Action dated Oct. 5, 2012, pertaining to U.S. Appl. No. 13/157,857, 12 pages.
Sunstein Kann Murphy & Timbers LLP, Amendment to Office Action dated Oct. 5, 2012, pertaining to U.S. Appl. No. 13/157,857, 10 pages.
United States Patent & Trademark Office, Office Action dated May 10, 2013, pertaining to U.S. Appl. No. 13/157,857, 6 pages.
Sunstein Kann Murphy & Timbers LLP, Request for Continued Examination and Response filed Nov. 11, 2013, pertaining to U.S. Appl. No. 13/157,857, 11 pages.
United States Patent & Trademark Office, Notice of Allowance dated Feb. 10, 2014, pertaining to U.S. Appl. No. 13/157,857, 5 pages.
United States Patent & Trademark Office, Office Action dated Oct. 27, 2014, pertaining to U.S. Appl. No. 13/887,712, 10 pages.
Sunstein Kann Murphy & Timbers LLP, Amendment to Office Action dated Oct. 27, 2014, pertaining to U.S. Appl. No. 13/887,712, 9 pages.
United States Patent & Trademark Office, Office Action dated May 28, 2015, pertaining to U.S. Appl. No. 13/887,712, 10 pages.
U.S. Appl. No. 10/160,667, filed May 28, 2002.
U.S. Appl. No. 10/681,750, filed Oct. 7, 2003.
U.S. Appl. No. 10/704,208, filed Nov. 7, 2003.
U.S. Appl. No. 10/997,407, filed Nov. 24, 2004.
U.S. Appl. No. 11/537,318, filed Sep. 29, 2006.
U.S. Appl. No. 11/688,340, filed Mar. 20, 2007.
U.S. Appl. No. 11/602,713, filed Nov. 21, 2006.
U.S. Appl. No. 12/398,871, filed Mar. 5, 2009.
U.S. Appl. No. 12/398,880, filed Mar. 5, 2009.
U.S. Appl. No. 12/464,763, filed May 12, 2009.
U.S. Appl. No. 12/777,809, filed May 11, 2010.
U.S. Appl. No. 12/778,506, filed May 12, 2010.
U.S. Appl. No. 12/778,518, filed May 12, 2010.
U.S. Appl. No. 12/799,299, filed Apr. 21, 2010.
U.S. Appl. No. 12/799,355, filed Apr. 22, 2010.
U.S. Appl. No. 12/799,641, filed Apr. 28, 2010.
U.S. Appl. No. 12/965,493, filed Dec. 10, 2010.
U.S. Appl. No. 13/294,564, filed Nov. 11, 2011.
U.S. Appl. No. 13/294,573, filed Nov. 11, 2011.
U.S. Appl. No. 13/294,579, filed Nov. 11, 2011.
U.S. Appl. No. 13/294,617, filed Nov. 11, 2011.
U.S. Appl. No. 13/294,623, filed Nov. 11, 2011.
U.S. Appl. No. 13/397,457, filed Feb. 15, 2012.
U.S. Appl. No. 13/399,378, filed Feb. 17, 2012.
U.S. Appl. No. 13/561,696, filed Jul. 30, 2012.
U.S. Appl. No. 13/565,840, filed Aug. 3, 2012.
U.S. Appl. No. 13/718,717, filed Dec. 18, 2012.

(56) References Cited

OTHER PUBLICATIONS

U.S. Appl. No. 13/718,735, filed Dec. 18, 2012.
U.S. Appl. No. 13/746,742, filed Jan. 22, 2013.
U.S. Appl. No. 13/761,818, filed Feb. 7, 2013.
U.S. Appl. No. 13/835,863, filed Mar. 15, 2013.
U.S. Appl. No. 13/886,040, filed May 2, 2013.
U.S. Appl. No. 13/887,712, filed May 6, 2013.
U.S. Appl. No. 13/938,081, filed Jul. 9, 2013.
U.S. Appl. No. 14/017,176, filed Sep. 3, 2013.
U.S. Appl. No. 14/040,890, filed Sep. 30, 2013.
U.S. Appl. No. 14/051,003, filed Oct. 10, 2013.
U.S. Appl. No. 14/051,087, filed Oct. 10, 2013.
U.S. Appl. No. 14/148,511, filed Jan. 6, 2014.
U.S. Appl. No. 14/157,707, filed Jan. 17, 2014.
European Patent Office, Partial Supplementary European Search Report—Application No. 13771863.1-1654, dated Apr. 26, 2016, 7 pages.
U.S. Appl. No. 14/033,095, filed Sep. 20, 2013.
U.S. Appl. No. 14/033,350, filed Sep. 20, 2013.
U.S. Appl. No. 14/216,473, filed Mar. 17, 2014.
U.S. Appl. No. 14/285,151, filed May 22, 2014.
U.S. Appl. No. 14/389,987, filed on Apr. 6, 2013.
U.S. Appl. No. 14/390,829, filed Apr. 13, 2013.
Sunstein Kann Murphy & Timbers LLP, Request for Continued Examination and Response filed Nov. 30, 2015, pertaining to U.S. Appl. No. 13/887,712, 10 pages.
United States Patent & Trademark Office, Office Action dated Mar. 7, 2016, pertaining to U.S. Appl. No. 13/887,712, 11 pages.
Sunstein Kann Murphy & Timbers LLP, Response to Office Action dated Mar. 7, 2016, pertaining to U.S. Appl. No. 13/887,712, 9 pages.
United States Patent & Trademark Office, Office Action dated Sep. 14, 2016, pertaining to U.S. Appl. No. 13/887,712, 10 pages.
United States Patent & Trademark Office, Office Action dated Nov. 2, 2010, pertaining to U.S. Appl. No. 12/031,239, 13 pages.
Sunstein Kann Murphy & Timbers LLP, Amendment to Office Action dated Nov. 2, 2010, pertaining to U.S. Appl. No. 12/031,239, 13 pages.
United States Patent & Trademark Office, Office Action dated Jun. 2, 2011, pertaining to U.S. Appl. No. 12/031,239, 8 pages.
Sunstein Kann Murphy & Timbers LLP, Request for Continued Examination and Response filed Dec. 2, 2011, pertaining to U.S. Appl. No. 12/031,239, 15 pages.
United States Patent & Trademark Office, Office Action dated Feb. 27, 2012, pertaining to U.S. Appl. No. 12/031,239, 8 pages.
Sunstein Kann Murphy & Timbers LLP, Amendment to Office Action dated Feb. 27, 2012, pertaining to U.S. Appl. No. 12/031,239, 7 pages.
United States Patent & Trademark Office, Notice of Allowance dated Oct. 12, 2012, pertaining to U.S. Appl. No. 12/031,239, 11 pages.
United States Patent & Trademark Office, Office Action dated Apr. 24, 2015, pertaining to U.S. Appl. No. 13/746,742, 7 pages.
Sunstein Kann Murphy & Timbers LLP, Response to Office Action dated Apr. 24, 2015, pertaining to U.S. Appl. No. 13/746,742, 10 pages.
United States Patent & Trademark Office, Notice of Allowance dated Apr. 11, 2016, pertaining to U.S. Appl. No. 13/746,742, 5 pages.
United States Patent & Trademark Office, Office Action dated Jul. 1, 2015, pertaining to U.S. Appl. No. 14/285,151, 8 pages.
Sunstein Kann Murphy & Timbers LLP, Response to Office Action dated Jul. 1, 2015, pertaining to U.S. Appl. No. 14/285,151, 9 pages.
United States Patent & Trademark Office, Office Action dated Feb. 19, 2016, pertaining to U.S. Appl. No. 14/285,151, 7 pages.
Sunstein Kann Murphy & Timbers LLP, Response to Office Action dated Feb. 19, 2016, pertaining to U.S. Appl. No. 14/285,151, 8 pages.
United States Patent & Trademark Office, Notice of Allowance dated Aug. 5, 2016, pertaining to U.S. Appl. No. 14/285,151, 5 pages.
Sunstein Kann Murphy & Timbers LLP, Amendment to Office Action dated Feb. 25, 2015, pertaining to U.S. Appl. No. 14/051,003, 8 pages.
United States Patent & Trademark Office, Notice of Allowance dated Mar. 14, 2016, pertaining to U.S. Appl. No. 14/051,003, 5 pages.
Japanese Patent Office, Office Action pertaining to Japanese Patent Application No. 2015-505970 dated Nov. 24, 2015, 2 pages ( in Japanese).
Japanese Patent Office, Office Action pertaining to Japanese Patent Application No. 2015-505970 dated Nov. 24, 2015, 4 pages (English translation).

* cited by examiner

IMPLANT DEVICE AND METHOD FOR MANUFACTURE

CROSS-REFERENCE TO RELATED APPLICATIONS

This application is a continuation of U.S. application Ser. No. 12/031,239, filed on Feb. 14, 2008, entitled "Implant Device and Method for Manufacture," which in turn claims the benefit of priority under 35 U.S.C. 119(e) to U.S. Application No. 60/889,859, filed on Feb. 14, 2007, entitled "Implant Device and Method for Manufacture."

U.S. application Ser. No. 12/031,239 is also a continuation-in-part of U.S. application Ser. No. 10/681,749 filed Oct. 7, 2003, entitled "Minimally Invasive Joint Implant with 3-Dimensional Geometry Matching the Articular Surfaces", which in turn claims priority to U.S. Application 60/416,601 filed Oct. 7, 2002, entitled "Minimally Invasive Joint Implant With 3-Dimensional Geometry Matching the Articular Surfaces," and U.S. Application 60/467,686 filed May 2, 2003, entitled "Joint Implants".

U.S. application Ser. No. 12/031,239 is also a continuation-in-part of U.S. application Ser. No. 10/997,407 filed Nov. 24, 2004, entitled "Patient Selectable Knee Joint Arthroplasty Devices"; which in turn is a continuation-in-part of U.S. application Ser. No. 10/752,438 filed Jan. 5, 2004, entitled "Patient Selectable Knee Joint Arthroplasty Devices"; which in turn is a continuation-in-part of U.S. application Ser. No. 10/724,010 filed Nov. 25, 2003, entitled "Patient Selectable Joint Arthroplasty Devices and Surgical Tools Facilitating Increased Accuracy, Speed and Simplicity in Performing Total and Partial Joint Arthroplasty"; which in turn is a continuation-in-part of U.S. application Ser. No. 10/305,652 filed Nov. 27, 2002, entitled "Methods and Compositions for Articular Repair"; which in turn is a continuation-in-part of U.S. application Ser. No. 10/160,667 filed May 28, 2002, entitled "Methods and Compositions for Articular Resurfacing"; which in turn claims the benefit of U.S. Application No. 60/293,488 filed May 25, 2001, entitled "Methods To Improve Cartilage Repair Systems", U.S. Application No. 60/363,527 filed Mar. 12, 2002, entitled "Novel Devices For Cartilage Repair", U.S. Application No. 60/380,695 filed May 14, 2002, entitled "Methods And Compositions for Cartilage Repair", and U.S. Application No. 60/380,692 filed May 14, 2002, entitled "Methods for Joint Repair".

The above-mentioned U.S. application Ser. No. 10/997,407 is also a continuation-in-part of U.S. application Ser. No. 10/681,750 filed Oct. 7, 2003, entitled "Minimally Invasive Joint Implant with 3-Dimensional Geometry Matching the Articular Surfaces".

All of the above patent applications, as well as patent applications and other references mentioned herein below, are hereby incorporated by reference in their entireties.

FIELD OF THE INVENTION

The present invention relates to orthopedic methods, systems and devices and more particularly, to joint implants and methods for manufacture.

BACKGROUND OF THE INVENTION

Joint implants are well known in the art. For example, one of the most common types of joint prosthetic devices is a knee implant including a femoral component and a tibial component. Other common joint implants are associated with, for example, the hip and shoulder.

The shape and size of various joint implants are becoming increasingly more complex and may include, for example, one or more concavities and/or convexities, as described in above-mentioned U.S. application Ser. No. 10/997,407. Traditional implant manufacturing processes, which may even include manual steps, and which may be satisfactory for less complex shaping, are becoming inadequate.

Furthermore, joint implants, such as a knee implant that includes tibial and femoral components, often require a relatively large cut on, for example, the tibia. This is due, in part, to the needed thickness (for strength and/or reliability) of the polyurethane tibial component. The cut on the tibia, upon which the tibial component rests, provides space for the needed thickness of the polyurethane tibial component, without overstuffing the joint. Such cuts are highly invasive, resulting in loss of bone stock, and over time, osteolysis frequently leads to loosening of the prosthesis. Further, the area where the implant and the bone mate degrades over time, requiring that the prosthesis be replaced. Since the patient's bone stock is limited, the number of possible replacement surgeries is also limited for joint arthroplasty.

SUMMARY OF THE INVENTION

One embodiment provides a method for making an implant suitable for a joint includes providing a blank with a (i.e., at least one) dimension smaller than the implant, and material is added to the blank so as to form surface detail on the implant. In related embodiments, adding material to the blank may include laser sintering and/or electron beam melting. Adding material to the block may include adding ceramic(s), metal(s) and/or ceramic-metal composite(s). The material added to the blank may be polished, also. In further embodiments, the blank may be made of, e.g., polymer(s), metal(s), cross-linked polymer(s), ceramic(s), ceramic-metal composite(s), and/or alloy(s); or use-appropriate combinations thereof. Providing the blank may include forming the blank by casting and/or milling. In still further embodiments, a three-dimensional shape of a (i.e., at least one, or a portion of at least one) surface of the joint is determined. Determining the three-dimensional shape may include the use of imaging, such as MRI, CT, ultrasound, digital tomosynthesis, and/or optical coherence techniques. The material added to the blank may be, in embodiments, such that a surface of the implant is a mirror image of a corresponding surface of the joint. The implant may be, e.g., a cartilage repair, unicompartmental knee, bicompartmental knee, total knee replacement, hip, shoulder, or interpositional joint implant. An interpositional joint implant may be associated with, e.g., a knee, hip or shoulder.

Another embodiment provides a method for making an implant suitable for a joint including providing a blank having a dimension that is different from the implant. The blank is modified using, at least in part, a laser, and/or electron beam melting to form the implant. The formed surfaces may desirably be polished. In related embodiments, the blank may include a dimension that is larger than the implant, and wherein modifying the blank includes cutting the blank with the laser. Laser-cut surfaces may desirably be polished. In further related embodiments, the blank may include a dimension that is smaller than the implant, and wherein modifying the blank includes adding material by laser sintering. The added material may be desirably polished. The blank may be made of polymer(s), metal(s), cross-linked polymer(s), ceramic(s), ceramic-metal composite(s), and/or alloy(s); or use-appropriate combinations thereof. The blank may be formed by casting and/or milling. In related embodiments, a three-dimensional shape of a (i.e., at least one, or a portion of at least one) surface of the joint may be determined. Determining the three-dimensional shape may include the use of imaging, such as MRI, CT, ultrasound, digital tomosynthesis, and/or optical coherence techniques. The blank may be desirably modified such that a surface of the implant is a mirror image of a corresponding surface of the joint.

In accordance with another embodiment, a method for making an implant suitable for a joint includes providing a blank with at least one dimension larger than the implant. A laser, polishing, etching, milling and/or an abrading process is used to cut the blank so as to form surface detail of the implant. In related embodiments, the blank may be made of polymer(s), metal(s), cross-linked polymer(s), ceramic(s), ceramic-metal composite(s), and/or alloy(s); or use-appropriate combinations thereof. Providing the blank may include forming the blank by casting and/or milling.

In still further embodiments, a three-dimensional shape of a (i.e., at least one, or a portion of at least one) surface of the joint is determined. Determining the three-dimensional shape may include the use of imaging, such as MRI, CT, ultrasound, digital tomosynthesis, and/or optical coherence. The blank may be desirably cut such that a surface of the implant is a mirror image of a corresponding surface of the joint. The implant may be, e.g., a cartilage repair, unicompartmental knee, bicompartmental knee, total knee replacement, hip, shoulder, or interpositional joint implant. An interpositional joint implant may be associated with, e.g., a knee, hip or shoulder.

In accordance with another embodiment, a knee implant includes a femoral component having first and second femoral component surfaces. The first femoral component surface is for securing to a surgically prepared compartment of a distal end of a femur. The second femoral component surface is configured to replicate the femoral condyle. The knee implant further includes a tibial component having first and second tibial component surfaces. The first tibial component surface is for contacting a proximal surface of the tibia that is substantially uncut subchondral bone (which may further include overlying articular cartilage.) At least a portion of the first tibial component surface is a mirror image of a corresponding proximal tibial surface. The second tibial component surface articulates with the second femoral component surface. In related embodiments, the second femoral component surface may include at least one of a ceramic and a metal, and the second tibial component surface may include ceramic(s) and/or metal(s). Both the second femoral component surface and the second tibial surface may include metal(s). Both the second femoral component surface and the second tibial surface may include ceramic(s).

The second femoral component surface may include one of a ceramic and a metal, and the second tibial surface may include the other of the one of a ceramic and a metal, e.g., the second femoral component surface may be ceramic, and the second tibial surface may be metal. The tibial component may have a thickness of 3 mm or less.

In related embodiments, the tibial component may include an anchoring mechanism, such as a peg and/or a keel. Alternatively, the tibial component may be an interpositional implant that does not include a physical anchoring mechanism.

BRIEF DESCRIPTION OF THE DRAWINGS

The foregoing features of the invention will be more readily understood by reference to the following detailed description, taken with reference to the accompanying drawings, in which.

DETAILED DESCRIPTION OF THE INVENTION AND EMBODIMENTS

The present invention is directed to methods for making joint implants that leverage additive or subtractive manufacturing methods including laser sintering and electron beam melting, and to non-invasive joint implants which may be advantageously made by the methods described herein. Such implants may feature a surface of the implant that is advantageously a mirror image of the joint surface. In another embodiment, non-invasive joint implants that rest on substantially uncut subchondral bone are described. The invention is now described in further detail, below.

As used herein and in the appended claims, the singular forms "a", "an", and "the" include plural references unless the context clearly dictates otherwise. Thus, for example, reference to "a device" includes a plurality of such devices and equivalents thereof known to those skilled in the art, and so forth. Similarly, the terms "a" (or "an"), "one or more" and "at least one" can be used interchangeably herein. Also, the terms "comprising", "including", and "having" can be used interchangeably.

It is to be understood that the implants described herein may be associated with a wide variety of joints, including, without limitation, joint implants used in a knee, shoulder, hip, vertebrae, elbow, ankle, hand, foot and wrist.

Figure 1:
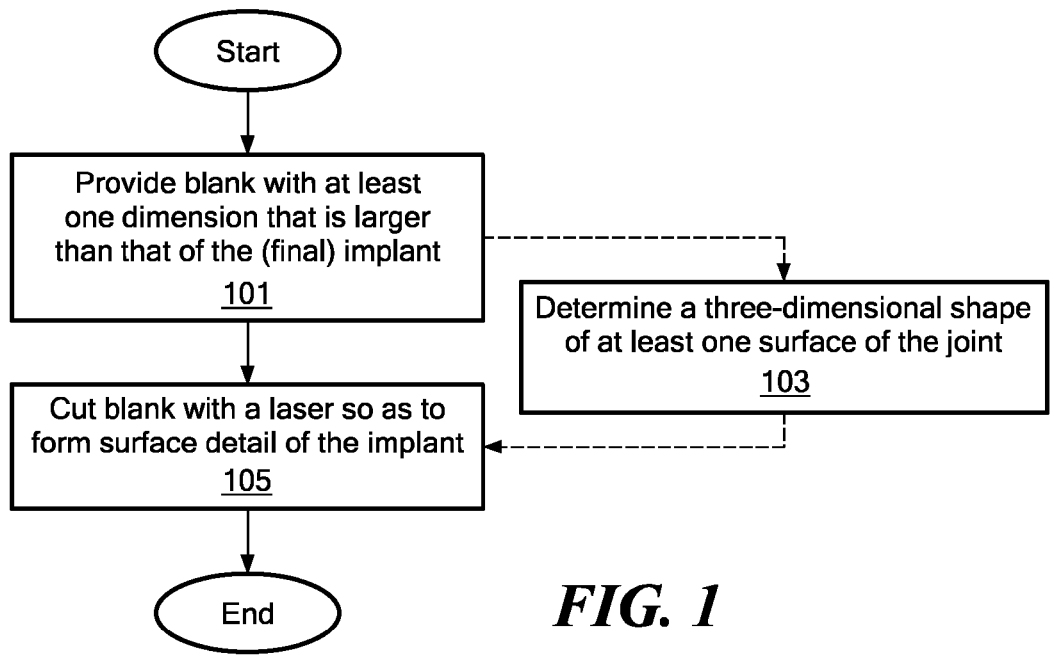
FIG. 1 is a flowchart depicting an embodiment of a method for manufacturing a joint implant.

FIG. 1 is a flowchart depicting a method for manufacturing a joint implant, in accordance with one embodiment of the invention. In step 101, a blank is provided with at least one dimension that is larger than that of the (final) implant. The dimension of the implant may be, e.g., a partial or uniform thickness, length, width, or curvature. The blank may be made, without limitation, a polymer, a metal, a cross-linked polymer, a ceramic, a ceramic-metal composite, and/or an alloy.

Suitable materials for use in joint implants and methods described herein can include metals and metal alloys including CoCrMo, CoCr, titanium alloys and commercially pure TI (cpTi), medical grade stainless steels, tantalum and tantalum alloys, and Nitinol ("NiTi"). Particularly advantageous materials are those well-suited, or specifically designed, for laser sintering or electron-beam melting manufacturing techniques, e.g., ASTM F-75 CoCr alloy, or Arcam Ti6Al4V ELI titanium alloy (available from Stratasys, Eden Prairie, Minn.) Ceramic materials, e.g., aluminum oxide or alumina, zirconium oxide or zirconia, compact of particulate diamond, and/or pyrolytic carbon may be used.

In various embodiments, the blank is dimensioned to be, in one or more portions, only slightly larger than that of the implant. For example, the blank may be milled or cast such that all, or certain portions of the blank, are only slightly larger than the implant. Providing a blank from which material will be removed to arrive at the precise implant size, geometry and surface characteristics, simplifies manufacturing processing and is believed to ensure reproducibility. The blank may be provided, e.g., by casting, milling, forging, compression molding, extruding or injection molding.

In various embodiments, a library of blanks may be kept of varying size and shapes. Upon determining an implant size, an appropriately sized blank may then be chosen.

Upon providing the blank, the blank is cut with a laser so as to form surface detail of the implant, step 105. Separately, or in addition to laser cutting, the blank may also be cut using precision milling or grinding, or other abrading processes known in the art. For example, after cutting the blank with the laser, the surface of the blank may desirably be polished.

In various embodiments, the method may further include determining a three-dimensional shape of at least one surface of the joint, step 103. Using the three-dimensional shape, the blank may be cut in step 105 such that a surface of the implant, or a portion thereof, is a mirror image of the corresponding joint surface (or portion thereof). For example, the implant surface may comprise a surface that is a mirror image of the joint surface to which the implant surface is designed to mate, so that the implant surface conforms to the joint surface, ensuring that the device fits the joint surface in precisely the correct location. The implant surface may alternately comprise more than one such mirror image surfaces, e.g., to assist in placement in the device, i.e., the implant surface need not comprise one contiguous mirror image of the joint surface. A series or pattern of smaller implant mirror image surfaces, each corresponding to or matching an area of the joint surface, can be provided. Without limitation, one application of this would be to provide grooves in which cement for affixing the device may be applied, so the device may be attached to the joint surface without flowing onto other areas of the implant surface. Another non-limiting application would be where a continuous conforming surface were not necessary, e.g., where the device may be properly seated by matching two, three, four or more conforming "reference surfaces" to corresponding areas of the joint surface. The area of the mirror image surface desirably should be sufficient to ensure that the device is located properly. Where there are more than one of these "reference surfaces", the area of each should be use- and application-appropriate, but a range of 1, 2, 3, 4, 5 $cm^2$ or more for each reference surface is contemplated. Where there is one implant surface with a mirror image, smaller areas comprising a mirror image are possible, as well as the entire implant surface. The joint surface may include at least one concavity and/or convexity.

Using the approach generally outlined in FIG. 1., a non-invasive joint implant, such as those described in above-mentioned U.S. application Ser. No. 10/997,407, may be manufactured. The implant may be, for example, a cartilage repair implant, a unicompartmental knee implant, a bicompartmental knee implant, a total knee replacement implant, a hip implant, and a shoulder implant. The implant may also be an interpositional implant, such as the implant described in above-mentioned U.S. Application No. 60/784,255.

Determining the three-dimensional shape of the joint surface may include a wide variety of imaging methodologies. For example, the imaging may include MRI, CT, ultrasound, digital tomosynthesis, and/or optical coherence. Reference is made to the above-mentioned U.S. application Ser. Nos. 10/997,407 and 10/728,731 for how imaging technologies are used to derive the three-dimensional shape of the joint surface. The 3-D information is then used in the CAD/CAM system to form the implant shape, geometry, and surfaces to make the desired implant.

Figure 2:
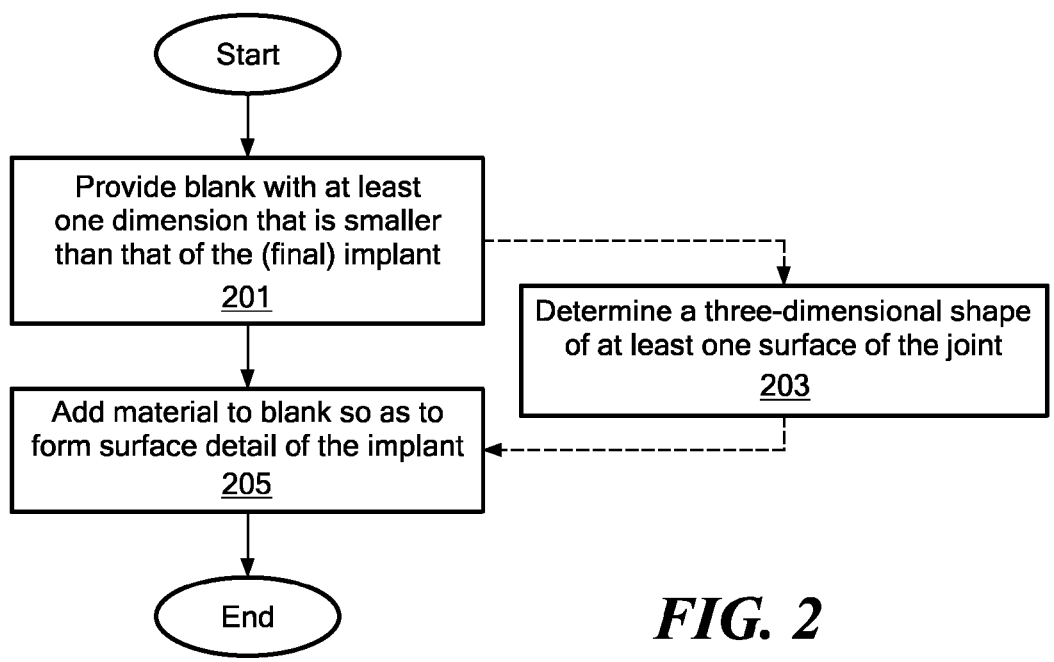
FIG. 2 is a flowchart depicting an embodiment of a method for manufacturing a joint implant.

FIG. 2 is a flowchart depicting a method for manufacturing a joint implant, in accordance with another embodiment. In step 201, a blank is provided with at least one dimension that is smaller than that of the (final) implant, instead of larger as described in FIG. 1. Material is then added to the block to form surface detail on the implant (step 205.)

The material may be added to the block using additive manufacturing technologies including laser sintering and/or electron beam melting. In laser sintering, a high power laser, such as a carbon dioxide laser, is used to fuse small particles of plastic, metal, or ceramic powders into a mass representing a desired three-dimensional object. Generally, the laser selectively fuses powdered material by scanning cross-sections generated from a 3-D digital description of the part (e.g., from a CAD file or scan data) on the surface of a powder bed. After each cross-section is scanned, the powder bed is lowered by one layer thickness, a new layer of material is applied on top, and the process is repeated until the part is completed. Laser sintering can produce parts from a relatively wide range of commercially available powder materials, including polymers, ceramics, and metals (such as steel, titanium, alloys and composites)

Full melting, partial melting, or liquid-phase sintering may be used. Electron beam melting involves melting or fusing metal, ceramic or other various powders, so as to build the part layer by layer. Exemplary electron beam melting systems are available from Stratasys, Eden Prairie, Minn.

After adding material to the blank, the surface of the blank may be desirably polished. Furthermore, and similar to above-described embodiments, the method may further include determining a three-dimensional shape of at least one surface of the joint, step 203. Using the three-dimensional shape, material may be added to the blank in step 205 such that at least one surface of the implant is a mirror image of at least one surface of the joint. The implant may be, for example, a cartilage repair implant, a unicompartmental knee implant, a bicompartmental knee implant, a total knee replacement implant, a hip implant, and a shoulder implant. The implant may also be an interpositional implant, such as the implant described in above-mentioned U.S. Application No. 60/784,255.

Determining the three-dimensional shape of the joint surface may include a wide variety of imaging methodologies. For example, the imaging may include MRI, CT, ultrasound, digital tomosynthesis, and/or optical coherence. Reference is made to the above-mentioned U.S. application Ser. Nos. 10/997,407 and 10/728,731 for how imaging technologies are used to derive the three-dimensional shape of the joint surface. The 3-D information is then used in the CAD/CAM system to form the implant shape, geometry, and surfaces to make the desired implant.

In accordance with another embodiment, a joint implant is presented wherein at least one surface of the implant rests on subchondral bone, and advantageously does not require invasive cutting of bone. These implants may be advantageously made by the methods described hereinabove. While an exemplary knee implant is described, it is to be understood that the joint implant may be associated with, for example, a shoulder, a hip, a vertebrae, an elbow, an ankle, a hand, a foot or a wrist.

Figure 3:
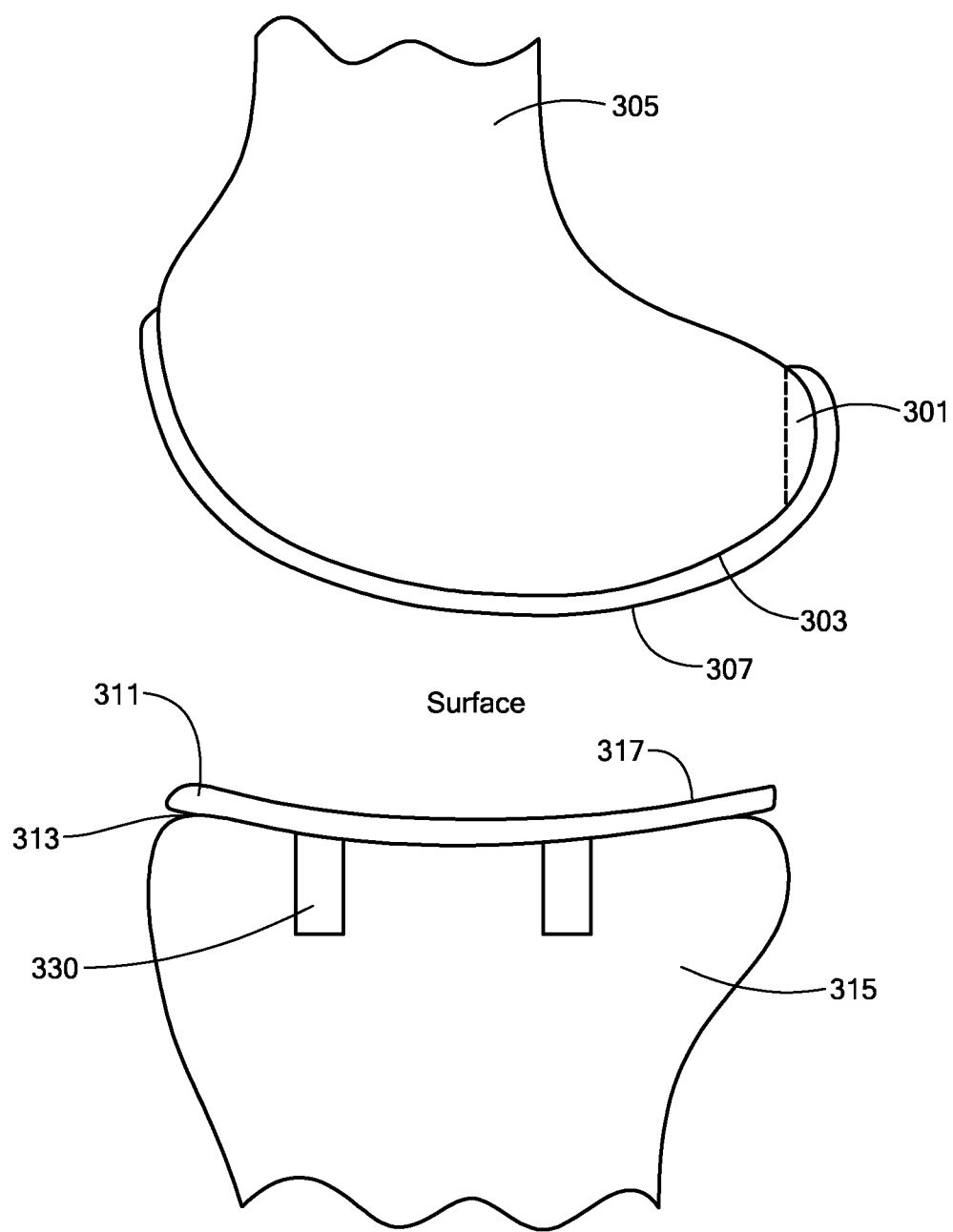
FIG. 3 shows an embodiment of a total knee implant, in cross-sectional view.

FIG. 3 shows in cross-section a total knee implant, in accordance with one embodiment. A femoral component 301 includes a first femoral component surface 303 for securing to a surgically prepared compartment of a distal end of a femur 305. A second femoral component surface 307 replicates the shape of the femoral condyle(s).

A tibial component 311 includes a first tibial component surface 313 for resting on and contacting a proximal surface of the tibia. The proximal surface of the tibia may advantageously include substantially uncut subchondral bone. In illustrative embodiments, at least a portion of the first tibial component surface 313 is a mirror image of the proximal surface. For example, a three-dimensional image of the proximal surface may be obtained as described above, with the first tibial component surface 313 manufactured based on the three-dimensional image. A second tibial component surface 317 articulates with the second femoral component surface 307. It is to be understood that in a total knee joint implant, the tibial component(s) cover both the medial and lateral plateau. In various embodiments, the tibial component may be a single component that covers both the medial and lateral plateau (and may or may not leave the tibial spines intact), or may include two components (i.e., a tibial component for the medial side and a tibial component for the lateral side). In other embodiments, for example, a unicondylar knee implant, the tibial component may cover either only the medial or lateral plateau.

In an exemplary embodiment, the femoral component 301 and the tibial component 311 may each be approximately 2-3 mm thick. The thickness may be, for example, similar to the thickness of cartilage removed in preparing the joint for implantation. Thus, overstuffing of the joint is minimized while providing a non-invasive alternative to traditional invasive knee surgery. Heretofore, such implants having the requisite dimensions and strength were not easily achievable. Some or all of the cartilage on the femoral and/or tibial articular surfaces may be removed to prepare the joint for receiving an implant (i.e., to expose some or all of the subchondral bone) as necessary, depending on the progression of cartilage wear, disease, etc. The interior surfaces of the femoral and/or tibial component may be accordingly designed so the implant may be affixed directly to the desired exposed area(s) of subchondral bone. The thickness and/or shape of the femoral and/or tibial components may be determined (e.g., so as to reconstruct the thickness of the originally present articular cartilage) from an image-derived subchondral bone shape of the joint surfaces, as described in the above-mentioned U.S. application Ser. No. 10/305,652.

To provide the required strength (e.g., for biomechanical loading) and reliability, and still be thin enough to avoid overstuffing the joint, the first tibial surface 313 and/or the second tibial surface 317 includes, without limitation, a metal and/or a ceramic. For example, the second femoral component surface 307 may includes at least one of a ceramic and a metal, and the second tibial component surface 317 includes at least one of a ceramic and a metal. In another example, both the second femoral component surface 307 and the second tibial surface 317 include a metal. In still another example, both the second femoral component surface 307 and the second tibial surface 317 include a ceramic. In yet another example, the second femoral component surface 307 includes one of a ceramic and a metal, and the second tibial surface 317 includes the other of the one of a ceramic and a metal.

In various embodiments, the knee implant includes an anchoring mechanism 330. The anchoring mechanism 330 may be, without limitation, a peg and a keel protruding from the first tibial surface 313.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated.

What is claimed is:

1. A method of manufacturing an implant for repairing a knee joint of a patient, wherein the implant includes a joint-facing surface and a bone-facing surface, the method comprising:
   a. deriving a three-dimensional shape of the knee joint of the patient from image data of the knee joint of the patient, wherein the image data include information about a shape, geometry or articular surface of a femoral condyle of the knee joint of the patient,
   b. providing a blank with at least one dimension larger than a corresponding dimension of the femoral condyle of the knee joint of the patient, wherein the blank is selected from a library of implants of various sizes and/or shapes; and
   c. altering the blank to obtain a desired shape of the joint-facing surface of the implant, wherein the desired shape replicates the femoral condyle of the knee joint of the patient in the corresponding dimension.

2. The method of claim 1, wherein the implant includes a medial condylar portion and a lateral condylar portion.

3. The method of claim 2, wherein the implant further includes a tibial component that provides both medial and lateral tibial plateaus.

4. The method of claim 3, including configuring the tibial component to leave tibial spines of the knee joint of the patient intact.

5. The method of claim 3, including configuring the tibial component not to leave tibial spines of the knee joint of the patient intact.

6. The method of claim 2, wherein the tibial component includes a first portion that provides a medial tibial plateau and a second portion that provides a lateral tibial plateau, wherein the first and second portions are separately formed.

7. The method of claim 1, including entering the three-dimensional shape into a CAD/CAM system.

8. The method of claim 7, wherein the CAD/CAM system is used to form the desired shape of the implant.

* * * * *